(12) United States Patent
Bureau et al.

(10) Patent No.: US 6,528,315 B2
(45) Date of Patent: Mar. 4, 2003

(54) METHOD FOR TRANSFERRING NUCLEIC ACID INTO MULTICELLED EUKARYOTIC ORGANISM CELLS AND COMBINATION THEREFOR

(75) Inventors: Michel Bureau, Saint Cloud (FR); Lluis Mir, Verrieres le Buisson (FR); Daniel Scherman, Paris (FR)

(73) Assignee: Aventis Pharma S.A., Antony Cedex (FR)

( * ) Notice: Subject to any disclaimer, the term of this patent is extended or adjusted under 35 U.S.C. 154(b) by 80 days.

(21) Appl. No.: 09/446,690

(22) PCT Filed: Jun. 30, 1998

(86) PCT No.: PCT/FR98/01399
§ 371 (c)(1),
(2), (4) Date: Feb. 2, 2000

(87) PCT Pub. No.: WO99/01157
PCT Pub. Date: Jan. 14, 1999

(65) Prior Publication Data
US 2002/0012914 A1 Jan. 31, 2002

Related U.S. Application Data
(60) Provisional application No. 60/067,487, filed on Dec. 1, 1997.

(30) Foreign Application Priority Data
Jun. 30, 1997 (FR) .............................. 97 08232

(51) Int. Cl.[7] .......................... C12N 15/87; C12Q 1/68; C12P 19/34; C07H 21/02; C07H 21/04
(52) U.S. Cl. .......................... 435/461; 435/6; 435/91.1; 435/455; 536/23.1; 536/24.5
(58) Field of Search .............................. 435/6; 536/23.1, 536/24.5, 455, 461; 514/44

(56) References Cited

U.S. PATENT DOCUMENTS

| | | | |
|---|---|---|---|
| 4,411,657 A | 10/1983 | Galindo |
| 4,441,972 A | 4/1984 | Pohl |
| 4,474,570 A | 10/1984 | Ariura et al. |
| 4,476,004 A | 10/1984 | Pohl |
| 4,557,723 A | 12/1985 | Sibalis |
| 4,578,168 A | 3/1986 | Hofmann |
| 4,622,031 A | 11/1986 | Sibalis |
| 4,639,244 A | 1/1987 | Rizk et al. |
| 4,663,292 A | 5/1987 | Wong et al. |
| 4,695,547 A | 9/1987 | Hilliard et al. |
| 4,702,732 A | 10/1987 | Powers et al. |
| 4,764,473 A | 8/1988 | Matschke et al. |
| 4,776,349 A | 10/1988 | Nashef et al. |
| 4,786,277 A | 11/1988 | Powers et al. |
| 5,019,034 A | 5/1991 | Weaver et al. |
| 5,049,488 A | 9/1991 | Baer et al. |
| 5,081,990 A | 1/1992 | Deletis |
| 5,119,832 A | 6/1992 | Xavier |
| 5,124,259 A | 6/1992 | Tada |
| 5,128,257 A | 7/1992 | Baer |
| 5,273,525 A | 12/1993 | Hofmann |
| 5,282,785 A | 2/1994 | Shapland et al. |
| 5,286,254 A | 2/1994 | Shapland et al. |
| 5,304,120 A | 4/1994 | Crandell et al. |
| 5,304,486 A | 4/1994 | Chang |
| 5,318,514 A | 6/1994 | Hofmann |
| 5,371,003 A | 12/1994 | Murray et al. |
| 5,389,069 A | 2/1995 | Weaver |
| 5,425,703 A | 6/1995 | Feiring |
| 5,439,440 A | 8/1995 | Hofmann |
| 5,462,520 A | 10/1995 | Hofmann |

(List continued on next page.)

FOREIGN PATENT DOCUMENTS

| | | |
|---|---|---|
| GB | 2113 097 A | 8/1983 |
| JP | 10-234366 | 8/1998 |
| WO | WO 89/06555 | 7/1989 |
| WO | WO 95/23211 | 8/1995 |
| WO | WO 96/00111 | 1/1996 |
| WO | WO 96/39531 | 12/1996 |
| WO | WO 97/07826 | 3/1997 |
| WO | WO 98/43702 | 10/1998 |
| WO | WO 99/06101 | 2/1999 |
| WO | WO 99/36563 | 7/1999 |
| WO | WO 00/02621 | 1/2000 |

OTHER PUBLICATIONS

Schofield et al. Brit. Med. Bull., vol. 51, No. 1, pp. 56–71, 1995.*
Crystal R.G. Science, vol. 210, pp. 239–242, 1995.*
Orkin et al. Report and Recommendation of the Panel to Assess the NIH Investment in Research on Gene Therapyl, 1995.*
Jolly, D. Cancer Gene Therapy, vol. 1, No. 1, pp. 51–64, 1995.*
Aihara et al., "Gene Transfer into Muscle by Electroporation In Vivo," *Nature Biotechnology*, 16, pp. 867–870 (1998).
Gorza et al., "Slow–to–Fast Transformation of Denervated Soleus Muscles by Chronic High–Frequency Stimulation in the Rat," *Journal of Physiology*, 402, pp. 627–649 (1988).
Heller et al., "In Vivo Gene Electroinjection and Expression in Rat Liver," *FEBS Letters*, 389, pp. 225–228 (1996).
Kim et al., "Electroporation of Extraneous Proteins into CHO Cells: Increased Efficacy by Utilizing Centrifugal Force and Microsecond Electrical Pulses," *Experimental Cell Research*, 197, pp. 207–212 (1991).
Lee et al., "Surfactant–induced Sealing of Electropermeabilized Skeletal Muscle Membranes In Vivo," *Proc. Natl. Acad. Sci. USA*, 89, pp. 4524–4528 (1992).

(List continued on next page.)

Primary Examiner—Sean McGarry
Assistant Examiner—Jane J Zara
(74) Attorney, Agent, or Firm—Finnegan, Henderson, Farabow, Garrett & Dunner, L.L.P.

(57) ABSTRACT

The invention concerns an improved method for transferring in vivo multicelled eukaryotic organism cells nucleic acids or nucleic acids combined with products for enhancing the efficacy of such transfers. The invention also concerns the combination of a nucleic acid and the transfer method for use in gene therapy.

46 Claims, 10 Drawing Sheets

U.S. PATENT DOCUMENTS

Figure 1A:
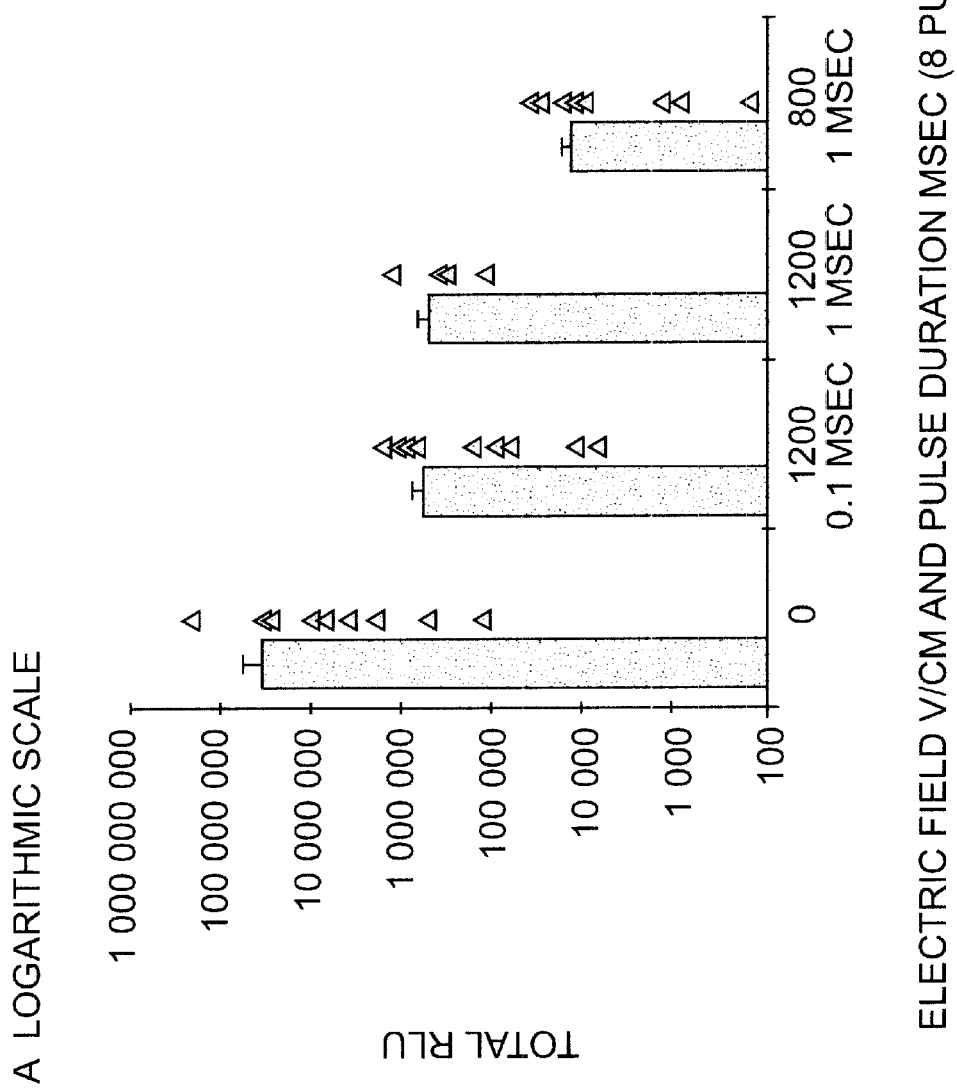

| | | | |
|---|---|---|---|
| 5,464,386 | A | 11/1995 | Hofmann |
| 5,468,223 | A | 11/1995 | Mir |
| 5,499,971 | A | 3/1996 | Shapland et al. |
| 5,501,662 | A | 3/1996 | Hofmann |
| 5,543,282 | A | 8/1996 | Mihayashi et al. |
| 5,589,069 | A | 12/1996 | Wenzhi |
| 5,607,691 | A | 3/1997 | Hale et al. |
| 5,662,944 | A | 9/1997 | Petrucco |
| 5,667,491 | A | 9/1997 | Pliquett et al. |
| 5,674,267 | A | 10/1997 | Mir et al. |
| 5,679,647 | A | 10/1997 | Carson et al. |
| 5,685,274 | A | 11/1997 | Helmbrecht et al. |
| 5,688,233 | A | 11/1997 | Hofmann et al. |
| 5,702,359 | A | 12/1997 | Hofmann et al. |
| 5,749,847 | A | 5/1998 | Zewert et al. |
| 5,804,566 | A | 9/1998 | Carson et al. |
| 5,810,762 | A | 9/1998 | Hofmann |
| 5,814,603 | A | 9/1998 | Oldenburg et al. |
| 5,849,719 | A | 12/1998 | Carson et al. |
| 5,944,710 | A | 8/1999 | Dev et al. |
| 5,944,726 | A | 8/1999 | Blaeser et al. |
| 5,960,974 | A | 10/1999 | Kee et al. |
| 5,993,434 | A | 11/1999 | Dev et al. |
| 6,014,584 | A | 1/2000 | Hofmann et al. |
| 6,055,453 | A | 4/2000 | Hofmann et al. |
| 6,110,161 | A | 8/2000 | Mathiesen et al. |

OTHER PUBLICATIONS

Mathiesen et. al., "Regulation of the Size and Distribution of Agrin–Induced Postsynaptic–like Apparatus in Adult Skeletal Muscle by Electrical Muscle Activity," *Molecular and Cellular Neuroscience*, 13, pp. 207–217 (1999).

Mathiesen, I., "Electropermeabilization of Skeletal Muscle Enhances Gene Transfer In Vivio," *Gene Therapy*, 5, pp. 508–514 (1999).

Nishi et al., "High–Efficiency In Vivo Gene Transfer Using Intraarterial Plasmid DNA Injection Following In Vivo Electroporation," *Cancer Research*, 56, pp. 1050–1055 (1996).

Rizzuto et al., "Efficient and Regulated Erythropoietin Production by Naked DNA Injection and Muscle Electroporation," *Proc. Natl. Acad. Si. USA*, 96, pp. 6417–6422 (1999).

Rols et al., "In Vivo Electrically Mediated Protein and Gene Transfer in Murine Melanoma," *Nature Biotechnology*, 16, pp. 168–170 (1998).

Rols et al., "Highly Efficient Transfection of Mammalian Cells by Electric Field Pulses," *Eur. J. Biochem.*, 206, pp. 115–121 (1992).

Sixou et al., "Optimized Conditions for Electrotransformation of Bacteria are Related to the Extent of Electropermeabilization," *Biochimica et Biophysica Acta*, 1088, pp. 135–138 (1991).

Tatham et al., "ATP–induced Pore Formation in the Plasma Membrane of Rat Peritoneal Mast Cells," *J. Gen Physiol.*, 95, pp. 459–476 (1990).

Teissie et al., "An Experimental Evaluation of the Critical Potential Difference Inducing Cell Membrane Electropermeabilization," *Biophysical Journal*, 65, pp. 409–413 (1993).

Titomirov et al., In Vivo Electroporation and Stable Transformation of Skin Cells of Newborn Mice by Plasmid DNA, *Biochimica et Biophysica Acta*, 1088, pp. 131–134 (1991).

* cited by examiner

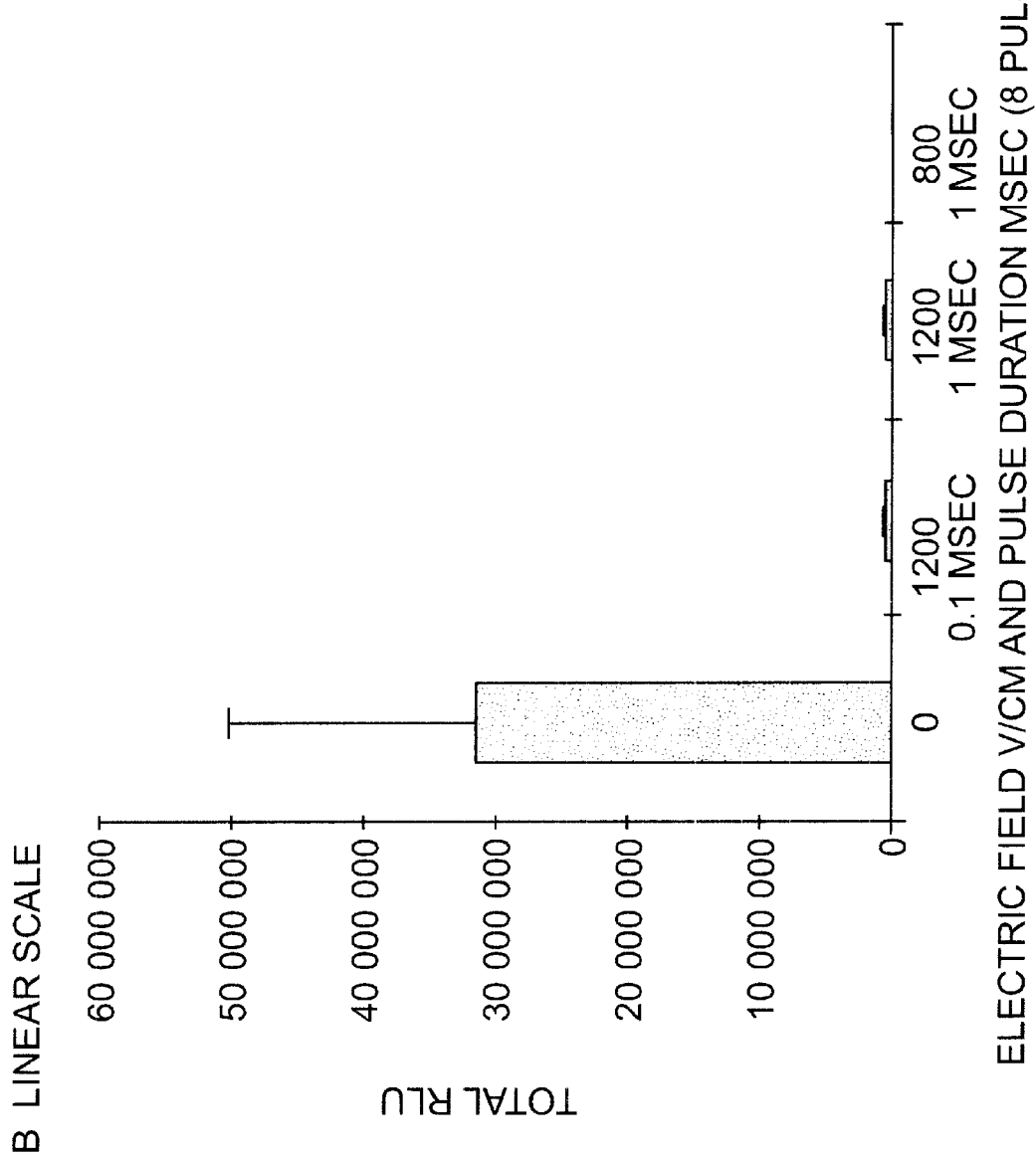

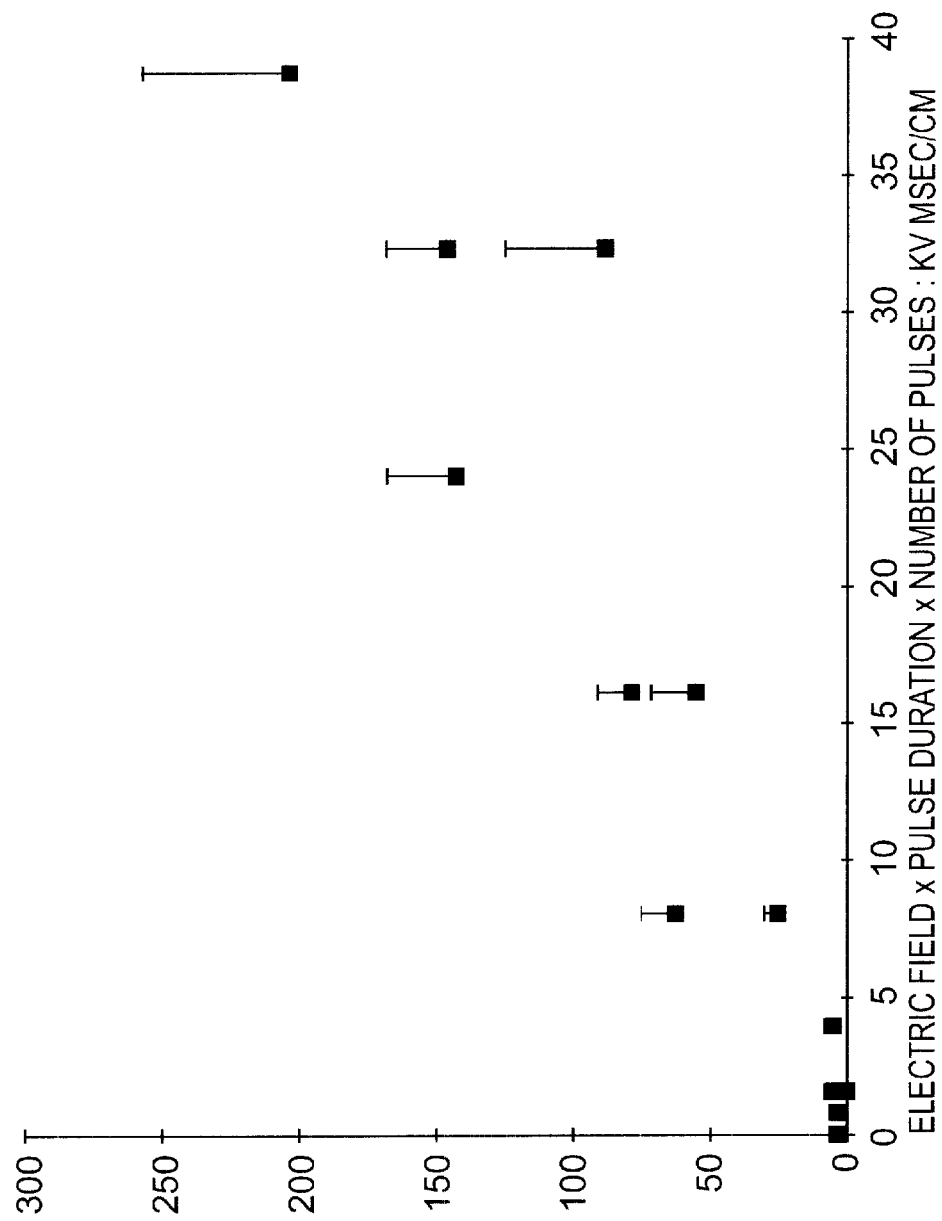

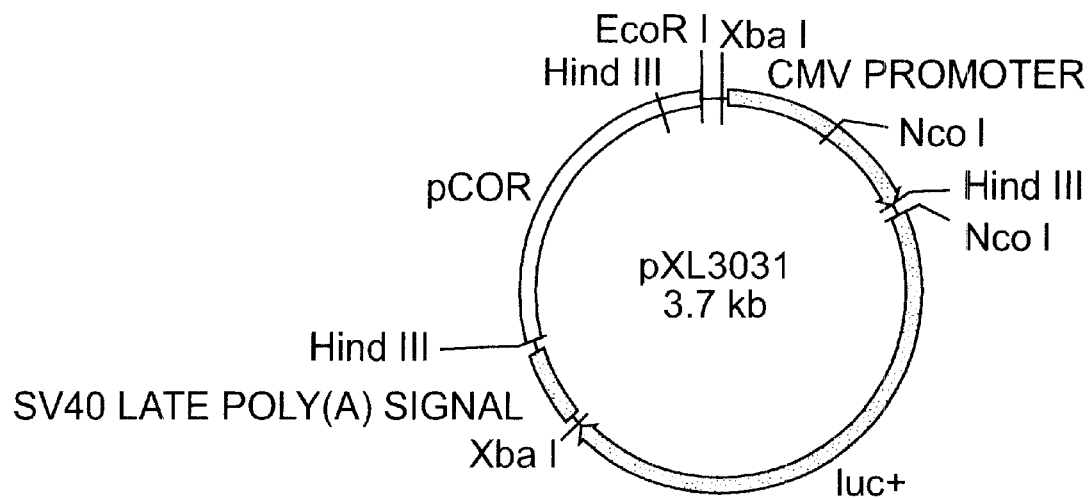
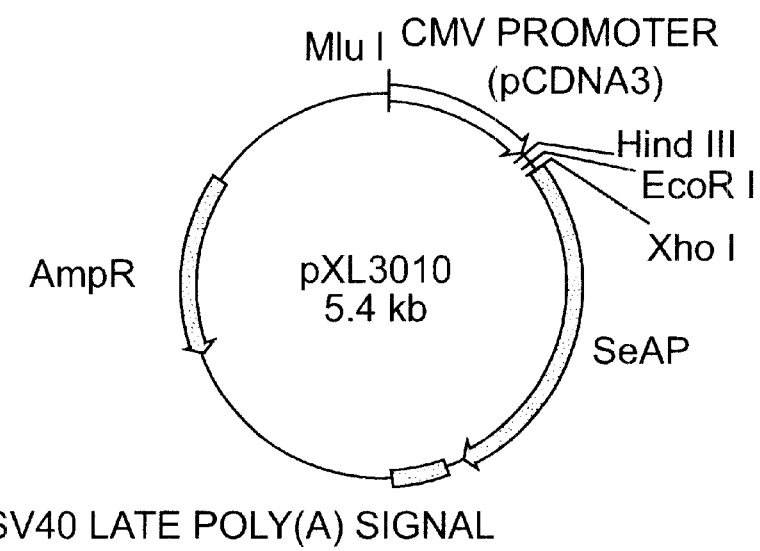
FIG. 6

METHOD FOR TRANSFERRING NUCLEIC ACID INTO MULTICELLED EUKARYOTIC ORGANISM CELLS AND COMBINATION THEREFOR

This application is a US National Stage application of co-pending PCT application PCT/FR98/01399, filed Jun. 30, 1998. This application also claims the benefit of domestic priority under 35 U.S.C. § 120 to application Ser. No. 60/067,487, filed Dec. 1, 1997 in the United States of America and the benefit of foreign priority under 35 U.S.C. § 119(a) to application FR97/08232, filed Jun. 30, 1997 in France.

The present invention relates to a very remarkable improvement in the in vivo transfer of nucleic acids into the cells of pluricellular eukaryotic organisms or of nucleic acids combined with products which make it possible to increase the yield of such transfers using weak electric fields of between 1 and 600 V/cm, and to the combination of a nucleic acid and the method of transfer according to the invention for their use in gene therapy.

The transfer of genes into a given cell is at the root of gene therapy. However, one of the problems is to succeed in causing a sufficient quantity of nucleic acid to penetrate into cells of the host to be treated; indeed, this nucleic acid, in general a gene of interest, has to be expressed in transfected cells. One of the approaches selected in this regard has been the integration of the nucleic acid into viral vectors, in particular into retroviruses, adenoviruses or adeno-associated viruses. These systems take advantage of the cell penetration mechanisms developed by viruses, as well as their protection against degradation. However, this approach has disadvantages, and in particular a risk of production of infectious viral particles capable of dissemination in the host organism, and, in the case of retroviral vectors, a risk of insertional mutagenesis. Furthermore, the capacity for insertion of a therapeutic or vaccinal gene into a viral genome remains limited.

In any case, the development of viral vectors capable of being used in gene therapy requires the use of complex techniques for defective viruses and for complementation cell lines.

Another approach (Wolf et al. Science 247, 1465–68, 1990; Davis et al. Proc. Natl. Acad. Sci. USA 93, 7213–18, 1996) has therefore consisted in administering into the muscle or into the blood stream a nucleic acid of a plasmid nature, combined or otherwise with compounds intended to promote its transfection, such as proteins, liposomes, charged lipids or cationic polymers such as polyethylenimine, which are good transfection agents in vitro (Behr et al. Proc. Natl. Acad. Sci. USA 86, 6982–6, 1989; Felgner et al. Proc. Natl. Acad. Sci. USA 84, 7413–7, 1987; Boussif et al. Proc. Natl. Acad. Sci. USA 92, 7297–301, 1995).

As regards the muscle, since the initial publication by J. A. Wolff et al. showing the capacity of muscle tissue to incorporate DNA injected in free plasmid form (Wolff et al. Science 247, 1465–1468, 1990), numerous authors have tried to improve this procedure (Manthorpe et al., 1993, Human Gene Ther. 4, 419–431; Wolff et al., 1991, BioTechniques 11, 474–485). A few trends emerge from these tests, such as in particular:

the use of mechanical solutions to force the entry of DNA into cells by adsorbing the DNA onto beads which are then propelled onto the tissues ("gene gun") (Sanders Williams et al., 1991, Proc. Natl. Acad. Sci. USA 88, 2726–2730; Fynan et al., 1993, BioTechniques 11, 474–485). These methods have proved effective in vaccination strategies but they affect only the top layers of the tissues. In the case of the muscle, their use would require a surgical approach in order to allow access to the muscle because the particles do not cross the skin tissues;

the injection of DNA, no longer in free plasmid form but combined with molecules capable of serving as vehicle facilitating the entry of the complexes into cells. Cationic lipids, which are used in numerous other transfection methods, have proved up until now disappointing, because those which have been tested have been found to inhibit transfection (Schwartz et al., 1996, Gene Ther. 3, 405–411). The same applies to cationic peptides and polymers (Manthorpe et al., 1993, Human Gene Ther. 4, 419–431). The only case of a favourable combination appears to be the mixing of poly(vinyl alcohol) or polyvinylpyrrolidone with DNA. The increase resulting from these combinations only represents a factor of less than 10 compared with DNA injected in naked form (Mumper et al., 1996, Pharmaceutical Research 13, 701–709);

the pretreatment of the tissue to be injected with solutions intended to improve the diffusion and/or the stability of DNA (Davis et al., 1993, Hum. Gene Ther. 4, 151–159), or to promote the entry of nucleic acids, for example the induction of cell multiplication or regeneration phenomena. The treatments have involved in particular the use of local anaesthetics or of cardiotoxin, of vasoconstrictors, of endotoxin or of other molecules (Manthorpe et al., 1993, Human Gene Ther. 4, 419–431; Danko et al., 1994, Gene Ther. 1, 114–121; Vitadello et al., 1994, Hum. Gene Ther. 5, 11–18). These pretreatment protocols are difficult to manage, bupivacaine in particular requiring, in order to be effective, being injected at doses very close to lethal doses. The preinjection of hyperosmotic sucrose, intended to improve diffusion, does not increase the transfection level in the muscle (Davis et al., 1993).

Other tissues have been transfected in vivo either using plasmid DNA alone or in combination with synthetic vectors (reviews by Cotten and Wagner (1994), Current Opinion in Biotechnology 4, 705; Gao and Huang (1995), Gene Therapy, 2, 710; Ledley (1995), Human Gene Therapy 6, 1129). The principal tissues studied were the liver, the respiratory epithelium, the wall of the vessels, the central nervous system and tumours. In all these tissues, the levels of expression of the transgenes have proved to be too low to envisage a therapeutic application (for example in the liver, Chao et al. (1996) Human Gene Therapy 7, 901), although some encouraging results have recently been obtained for the transfer of plasmid DNA into the vascular wall (Iires et al. (1996) Human Gene Therapy 7,959 and 989). In the brain, the transfer efficiency is very low, likewise in tumours (Schwartz et al. 1996, Gene Therapy 3, 405; Lu et al. 1994, Cancer Gene Therapy 1, 245; Son et al. Proc. Natl. Acad. Sci. USA 91, 12669).

Electroporation, or use of electric fields to permeabilize cells, is also used in vitro to promote the transfection of DNA into cells in culture. However, it has up until now been accepted that this phenomenon responded to an effect which is dependent on a threshold and that this electropermeabilization could only be observed for electric fields of relatively high intensity, of the order of 800 to 1200 volts/cm for animal cells. This technique has also been proposed in vivo to improve the efficacy of antitumour agents, such as bleomycin, in solid tumours in man (American Patent No. 5, 468,228, L. M. Mir). With pulses of very short duration (100 microseconds), these electrical conditions (800 to 1200 volts/cm) are very well suited to the intracellular transfer of small molecules. These conditions (pulses of 100 microseconds) have been applied with no improvement for the transfer of nucleic acids in vivo into the liver, where fields of less than 1000 volts/cm have proved completely ineffective, and even inhibitory compared with the injection of DNA in the absence of electrical impulses (Patent WO 97/07826 and Heller et al. FEBS Letters, 389, 225–8, 1996).

There are in fact difficulties with applying this technique in vivo because the administration of fields of such an intensity may cause extensive tissue lesions to a greater or lesser extent which do not represent a problem for the treatment of cancer patients but which may have a major disadvantage for the healthy subject or the sick subject when the nucleic acid is administered into tissues other than tumour tissues.

Whereas all the studies cited mention the need for high electric fields, of the order of 1000 volts/cm, to be effective in vivo, in a truly unexpected and remarkable manner, the applicants have now shown that the transfer of nucleic acids into tissues in vivo could be very substantially increased, without undesirable effects, by subjecting the tissue to electrical pulses of low intensity, for example 100 or 200 volts/cm and of a relatively long duration. Furthermore, the applicants have observed that the high variability in the expression of the transgene observed in the prior art for the transfer of DNA was notably reduced by the method according to the invention.

Accordingly, the present invention relates to a method of transferring nucleic acids in vivo, in which the cells of the tissues are brought into contact with the nucleic acid to be transferred, by direct administration into the tissue or by topical or systemic administration, and in which the transfer is brought about by application to the said tissues of one or more electrical pulses of an intensity between 1 and 600 volts/cm.

According to a preferred mode, the method according to the invention applies to tissues whose cells have specific geometries, such as for example cells of large size and/or of elongated shape and/or naturally responding to electrical action potentials and/or having a specific morphology.

Preferably, the intensity of the field is between 200 and 600 volts/cm and the total duration of application is greater than 10 milliseconds. The number of pulses used is, for example, from 1 to 100,000 pulses and the frequency of the pulses is between 0.1 and 1000 Hertz. Preferably, the frequency of the pulses is between 0.2 and 100 Hertz. The pulses may also be delivered in an irregular manner and the function which describes the intensity of the field as a function of time may be variable. By way of example, the electric field delivered may result from the combination of at least one field of an intensity >400 V/cm and preferably of between 500 and 800 Volts/cm, of short unit duration (<1 msec), followed by one or more pulses of lower intensity, for example <400 Volts/cm, and preferably <200 Volts/cm and of longer unit duration (>1 msec). The integral of the function describing the variation of the electric field with time is greater than 1 kV×msec/cm. According to a preferred mode of the invention, this integral is greater than or equal to 5 kV×msec/cm.

According to a preferred mode of the invention, the field intensity of the pulses is approximately 500 volts/cm (i.e. ±10% and preferably ±5%).

The electrical pulses are chosen from square wave pulses, electric fields generating exponentially decreasing waves, oscillating unipolar waves of limited duration, oscillating bipolar waves of limited duration, or other wave forms. According to a preferred mode of the invention, the electrical pulses are square wave pulses.

The administration of electrical pulses may be carried out by any method known to persons skilled in the art, for example:
   system of external electrodes placed on either side of the tissue to be treated, in particular non-invasive electrodes placed in contact with the skin,
   system of electrodes implanted in the tissues,
   system of electrodes/injector allowing the simultaneous administration of the nucleic acids and the electric field.

Within the framework of the present invention, the terms transfer of DNA or of nucleic acids by application of one or more electrical pulses, as well as the terms electrotransfer or alternatively electrotransfection should be considered as equivalent and designate the transfer of nucleic acids or of DNA by application or in the presence of an electric field.

The administration being carried out in vivo, it is sometimes necessary to use intermediate products which provide electrical continuity with non-invasive external electrodes. This may be for example an electrolyte in gel form.

The nucleic acids may be administered by any appropriate means, but are preferably injected in vivo directly into the tissues or administered by another route, local or systemic and in particular by means of a catheter, which makes them available at the site of application of the electric field. The nucleic acids may be administered with agents allowing or facilitating transfer, as was mentioned above. In particular, these nucleic acids may be free in solution or combined with synthetic agents, or carried by viral vectors. The synthetic agents may be lipids or polymers known to a person skilled in the art, or alternatively targeting elements allowing attachment to the membrane of the target tissues. Among these elements, there may be mentioned vectors carrying sugars, peptides, antibodies or hormone receptors.

It can be understood, under these conditions of the invention, that the administration of the nucleic acids can be preceded by, simultaneous with or even subsequent to the application of the electric fields.

Accordingly, the subject of the present invention is also a nucleic acid and an electric field of an intensity between 1 and 600 volts/cm, as combination product for their administration simultaneously, separately or spaced out over time, to mammalian cells and in particular human cells, in vivo. Preferably, the intensity of the field is between 200 and 600 volts/cm and, more preferably still, the intensity of the field is approximately 500 volts/cm.

The method according to the present invention can be used in gene therapy, that is to say therapy in which the expression of a transferred gene, but also the modulation or the blocking of a gene, makes it possible to provide the treatment of a particular pathological condition.

Preferably, the cells of the tissues are treated for the purpose of a gene therapy allowing:
   either the correction of dysfunctions of the cells themselves (for example for the treatment of diseases linked to genetic deficiencies such as for example cystic fibrosis),
   or the safeguard and/or the regeneration of the vascularization or the innervation of the tissues or organs by trophic, neurotrophic and angiogenic factors produced by the transgene,
   or the transformation of the tissue into an organ secreting products leading to a therapeutic effect such as the product of the gene itself (for example factors for regulation of thrombosis and of haemostasis, trophic factors, hormones) or such as an active metabolite synthesized in the tissue by virtue of the addition of the therapeutic gene, or a vaccine or immunostimulant application.

Another subject of the invention is the combination of the electrical pulses of a field with compositions containing nucleic acids formulated for any administration allowing access to the tissue by the topical, cutaneous, oral, vaginal, parenteral, intranasal, intravenous, intra-arterial, intramuscular, subcutaneous, intraocular or transdermal route, and the like. Preferably, the pharmaceutical compositions of the invention contain a pharmaceutically acceptable vehicle for an injectable formulation, in particular for a direct injection into the desired organ, or for any other administration. They may be in particular isotonic sterile solutions or dry, in particular freeze-dried, compositions which, upon addition, depending on the case, of sterilized water or of physiological saline, allow the preparation of injectable solutions. The nucleic acid doses used for the injection as well as the number of administrations and the volume of injections may be adjusted according to various parameters, and in particular according to the mode of administration used, the relevant pathological condition, the gene to be expressed, or the desired duration of treatment.

The nucleic acids may be of synthetic or biosynthetic origin, or may be extracted from viruses or prokaryotic cells or from eukaryotic cells derived from unicellular organisms (for example yeasts) or from pluricellular organisms. They may be administered in combination with all or part of the components of the organism of origin and/or of the synthesis system.

The nucleic acid may be a deoxyribonucleic acid or a ribonucleic acid. It may be sequences of natural or artificial origin, and in particular genomic DNA, cDNA, mRNA, tRNA and rRNA, hybrid sequences or synthetic or semisynthetic sequences of modified or unmodified oligonucleotides. These nucleic acids may be obtained by any technique known to persons skilled in the art, and in particular by targeting libraries, by chemical synthesis or by mixed methods including chemical or enzymatic modification of sequences obtained by targeting libraries. They may be chemically modified.

In particular, the nucleic acid may be a DNA or a sense or antisense RNA or an RNA having catalytic property such as a ribozyme. "Antisense" is understood to mean a nucleic acid having a sequence complementary to a target sequence, for example an mRNA sequence the blocking of whose expression is sought by hybridization with the target sequence. "Sense" is understood to mean a nucleic acid having a sequence which is homologous or identical to a target sequence, for example a sequence which binds to a protein transcription factor and which is involved in the expression of a given gene. According to a preferred embodiment, the nucleic acid comprises a gene of interest and elements allowing the expression of the said gene of interest. Advantageously, the nucleic acid fragment is in the form of a plasmid.

The deoxyribonucleic acids may be single- or double-stranded, as well as short oligonucleotides or longer sequences. They may carry therapeutic genes, sequences for regulation of transcription or of replication, or regions for binding to other cellular components, and the like. For the purposes of the invention, "therapeutic gene" is understood to mean in particular any gene encoding an RNA or a protein product having a therapeutic effect. The protein product encoded may be a protein, a peptide and the like. This protein product may be homologous in relation to the target cell (that is to say a product which is normally expressed in the target cell when the latter exhibits no pathological condition). In this case, the expression of the transgene makes it possible, for example, to overcome an inadequate expression in the cell or the expression of an inactive or weakly active protein due to a modification, or makes it possible to overexpress the said protein. The therapeutic gene may also encode a mutant of a cellular protein having increased stability or a modified activity, and the like. The protein product may also be heterologous in relation to the target cell. In this case, an expressed protein may, for example, supplement or provide an activity which is deficient in the cell (treatment of enzymatic deficiencies), or may make it possible to combat a pathological condition, or to stimulate an immune response for example for the treatment of tumours. It may be a suicide gene (Herpes Thymidine Kinase) for the treatment of cancers or of restenosis.

Among the therapeutic products for the purposes of the present invention, there may be mentioned more particularly the genes encoding enzymes, such as α-1-antitrypsin, proteinase (metalloproteinases, urokinase, uPA, tPA, . . . streptokinase), proteases cleaving precursors in order to liberate active products (ACE, ICE, . . . ), or their antagonists (TIMP-1, tissue plasminogen activator inhibitor PAI, TFPI blood derivatives such as the factors involved in coagulation: factors VII, VIII, IX, complement factors, thrombin, hormones, or enzymes involved in the pathway for the synthesis of hormones, or factors involved in controlling the synthesis or the excretion or the secretion of hormones, such as insulin, factors close to insulin (IGF), or growth hormone, ACTH, enzymes for the synthesis of sex hormones, lymphokines and cytokines: interleukins, chemokines (CXC and CC), interferons, TNF, TGF, chemotactic factors or activators such as MIF, MAF, PAF, MCP-1, eotaxin, LIF, and the like (French Patent No. 92 03120), growth factors, for example IGF, EGF, FGF, KGF, NGF, PDGF, PlGF, HGF, proliferin angiogenic factors such as VEGF of FGF, angiopoietin 1 or 2, endothelin enzymes for synthesizing neurotransmitters, trophic factors, in particular neurotrophic factors for the treatment of neurodegenerative diseases, traumas which have damaged the nervous system, or retinal degeneration, such as members of the family of neurotrophins such as NGF, BDNF, NT3, NT4/5, NT6, their derivatives and related genes—members of the CNTF families such as CNTF, axokine, LIF and derivatives thereof—IL6 and its derivatives—cardiotrophin and its derivatives—GDNF and its derivatives—members of the family of IGFs, such as IGF-1, IFGF-2 and derivatives thereof—members of the FGF family, such as FGF 1, 2, 3, 4, 5, 6, 7, 8, 9 and derivatives thereof, TGFβ bone growth factors, haematopoietic factors, such as erythropoietin, GM-CSF, M-CSF, LIF, and the like, cellular architectural proteins such as dystrophin or minidystrophin (French Patent No. 91 11947),, suicide genes (thymidine kinase, cytosine deaminase, cytochrome P450-containing enzymes), genes for haemoglobin or other protein carriers, genes corresponding to the proteins involved in the metabolism of lipids, of the apolipoprotein type chosen from apolipoproteins A-I, A-II, A-IV, B, C-I, C-II, C-III, D, E, F, G, H, J and apo(a), metabolic enzymes such as, for example, lipases, lipoprotein lipase, hepatic lipase, lecithin-cholesterol acyltransferase, 7-alpha-cholesterol hydroxylase, phosphatidyl acid phosphatase, or alternatively lipid transfer proteins such as the cholesterol ester transfer protein and the phospholipid transfer protein, an HDL-binding protein or alternatively a receptor chosen, for example, from the LDL receptors, the remnant chylomicron receptors and the scavenger receptors, and the like. It is furthermore possible to add leptin for the treatment of obesity.

blood pressure regulating factors, such as the enzymes involved in the metabolism of NO, angiotensin, bradykinin, vasopressin, ACE, renin, the enzymes encoding the mechanisms for the synthesis or for the relief of prostaglandins, thromboxan, or adenosine, adenosine receptors, kallikreins and kallistatins, ANP, ANF, diuretic or antidiuretic factors, factors involved in the synthesis, the metabolism or the release of mediators such as histamine, serotonin, catecholamines, neuropeptides, anti-angiogenic factors such as the ligand for Tie-1 and for Tie-2, angiostatin, ATF factor, derivatives of plasminogen, endothelin, thrombospondins 1 and 2, PF-4, α- or β-interferon, interleukin-12, TNFα, urokinase receptor, flt1, KDR, PAI1, PAI2, TIMP1, prolactin fragment, factors protecting against apoptosis, such as the AKT family, proteins capable of inducing cell death, either active by themselves such as the caspases or of the "pro-drug" type requiring activation by other factors, or proteins activating pro-drugs into an agent causing cell death, such as the herpesvirus thymidine kinase, deaminases, which make it possible in particular to envisage anti-cancer therapies, proteins involved in intercellular contacts and adhesion: VCAM, PECAM, ELAM, ICAM, integrins, cathenins, proteins of the extracellular matrix, proteins involved in the migration of cells proteins of the signal transduction type, of the type including FAK, MEKK, p38 kinase, tyrosines, kinases, serine-threonine kinases, proteins involved in the regulation of the cell cycle (p21, p16, cyclines, . . . ) as well as the dominant negative mutant or derived proteins blocking the cell cycle and capable, where appropriate, of inducing apoptosis.

transcription factors: jun, fos, AP1, p53, . . . and the proteins of the p53 signalling cascade.

cell structure proteins, such as the intermediate filaments (vimentin, desmin, keratins), dystrophin, the proteins involved in muscle contractility and in controlling muscle contractibility, in particular the proteins involved in calcium metabolism and the flow of calcium in the cells (SERCA, . . . ).

In the cases of proteins which function through ligand and receptor systems, it is possible to envisage using the ligand or the receptor (e.g. FGF-R, VEGR-R, . . . ). It is also possible to mention genes encoding fragments or mutants of ligand or receptor proteins, in particular of the abovementioned proteins, either having an activity greater than the whole protein, or an antagonist activity, or even an activity of the "dominant negative" type relating to the initial protein (for example fragments of receptors inhibiting the availability of circulating proteins, associated or otherwise with sequences inducing secretion of these fragments in relation to anchorage in the cell membrane, or other systems for modifying the intracellular traffic of these ligand-receptor systems so as to divert the availability of one of the elements) or even possessing an inherent activity distinct from that of the total protein (e.g. ATF).

Among the other proteins or peptides which may be secreted by the tissue, it is important to underline antibodies, the variable fragments of single-chain antibody (ScFv) or any other antibody fragment possessing recognition capacities for its use in immunotherapy, for example for the treatment of infectious diseases, of tumours, of autoimmune diseases such as multiple sclerosis (antiidiotype antibodies) as well as the ScFv's which becomes attached to the pro-inflammatory cytokines such as, for example, IL1 and TNFα for the treatment of rheumatoid arthritis. Other proteins of interest are, in a nonlimiting manner, soluble receptors such as, for example, the soluble CD4 receptor or the soluble receptor for TNF for anti-HIV therapy, the TNFα receptor or the IL1 soluble receptor for the treatment of rheumatoid arthritis, the soluble receptor for acetylcholine for the treatment of myasthenia; substrate peptides or enzyme inhibitors, or peptides which are agonists or antagonists of receptors or of adhesion proteins such as, for example, for the treatment of asthma, thrombosis, restenosis, metastasis or inflammation; artificial, chimeric or truncated proteins. Among the hormones of essential interest, there may be mentioned insulin in the case of diabetes, growth hormone and calcitonin. It is also possible to mention proteins capable of inducing antitumour immunity or of stimulating the immune response (IL2, GM-CSF, IL12, and the like). Finally, it is possible to mention the cytokines which reduce the $T_{H1}$ response such as IL10, IL4 and Il13.

The numerous examples which precede and those which follow illustrate the potential scope of the field of application of the present invention.

The therapeutic nucleic acid may also be an antisense sequence or gene whose expression in the target cell makes it possible to control the expression of genes or the transcription of cellular mRNAs. Such sequences may, for example, be transcribed in the target cell into RNA complementary to cellular mRNAs and thus block their translation into protein, according to the technique described in European Patent No. 140 308. The therapeutic genes also comprise the sequences encoding ribozymes, which are capable of selectively destroying target RNAs (European Patent No. 321 201).

As indicated above, the nucleic acid may also comprise one or more genes encoding an antigenic peptide capable of generating an immune response in humans or in animals. In this particular embodiment, the invention therefore allows either the production of vaccines, or the carrying out of immunotherapeutic treatments applied to humans or to animals, in particular against microorganisms, viruses or cancers. It may be in particular antigenic peptides specific for the Epstein-Barr virus, the HIV virus, the hepatitis B virus (European Patent No. 185 573), the pseudo-rabies virus, the "syncytia forming virus", other viruses or antigens specific for tumours such as the MAGE proteins (European Patent No. 259 212), such as MAGE 1, MAGE 2 proteins or antigens which can stimulate an anti-tumour response such as bacterial heat shock proteins.

Preferably, the nucleic acid also comprises sequences allowing and/or promoting the expression, in the tissue, of the therapeutic gene and/or of the gene encoding the antigenic peptide. They may be sequences which are naturally responsible for the expression of the gene considered when these sequences are capable of functioning in the transfected cell. They may also be sequences of different origin (responsible for the expression of other proteins, or even synthetic). In particular, they may be promoter sequences of eukaryotic or viral genes. For example, they may be promoter sequences derived from the genome of the cell which it is desired to transfect. Among the eukaryotic promoters, there may be mentioned any promoter or derived sequence stimulating or repressing the transcription of a gene in a specific manner or otherwise, strongly or weakly. They may be in particular ubiquitous promoters (HPRT, vimentin, α-actin, tubulin, and the like), promoters of therapeutic genes (of the type including MDR, CFTR, and the like), tissue-specific promoters (of the type including promoters of genes for desmin, myosins, creatine kinase, phosphoglycerate kinase) or alternatively promoters responding to a stimulus such as promoters responding to the natural hormones (receptor for steroid hormones, receptor for retinoic acid, and the like) or a promoter regulated by antibiotics (tetracyclin, rapamycin, and the like), promoters responding to a dietary regimen such as the promoters responding to fibrates, or other promoters responding to other molecules of natural or synthetic origin. Likewise, they may be promoter sequences derived from the genome of a virus. In this regard, there may be mentioned, for example, the promoters of the EIA genes of the adenovirus, MLP genes, or promoters derived from genomes of the viruses CMV, RSV, SV40, and the like. The promoters may also be inducible or repressible. In addition, these expression sequences may be modified by the addition of activating or regulatory sequences, allowing a conditional or transient expression, a tissue-specific or predominant expression, and the like.

Moreover, the nucleic acid may also comprise, in particular upstream of the therapeutic gene, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also comprise a signal sequence directing the synthesized therapeutic product towards a particular compartment of the cell, such as, for example, peroxisomes, lysosomes and mitochondria for the treatment, for example, of mitochondrial genetic diseases.

Other genes which are of interest have been described in particular by McKusick, V. A. Mendelian (Inheritance in man, catalogs of autosomal dominant, autosomal recessive, and X-linked phenotypes. Eighth edition, John Hopkins University Press (1988)), and in Stanbury, J. B. et al. (The metabolic basis of inherited disease, Fifth edition, McGraw-Hill (1983)). The genes of interest cover the proteins involved in the metabolism of amino acids, lipids and other constituents of the cell.

There may thus be mentioned, with no limitation being implied, the genes associated with diseases of carbohydrate metabolism such as for example fructose-1-phosphate aldolase, fructose-1,6-diphosphatase, glucose-6-phosphatase, lysosomal α-1,4-glucosidase, amylo-1,6-glucosidase, amylo-(1,4:1,6)-transglucosidase, muscle phosphorylase, muscle phosphofructokinase, phosphorylase-β-kinase, galactose-1-phosphate uridyl transferase, all the enzymes of the complex pyruvate dehydrogenase, pyruvate carboxylase, 2-oxoglutarate glyoxylase carboxylase, D-glycerate dehydrogenase.

There may also be mentioned:

the genes associated with diseases of amino acid metabolism such as for example phenylalanine hydroxylase, dihydrobiopterin synthetase, tyrosine aminotransferase, tyrosinase, histidinase, fumarylacetoacetase, glutathione synthetase, γ-glutamylcysteine synthetase, ornithine-δ-aminotransferase, carbamoylphosphate synthetase, ornithine carbamoyltransferase, argininosuccinate synthetase, argininosuccinate lyase, arginase, L-lysine dehydrogenase, L-lysine ketoglutarate reductase, valine transaminase, leucine isoleucine transaminase, decarboxylase for the branched-chain 2-keto acids, isovaleryl-CoA dehydrogenase, acyl-CoA dehydrogenase, 3-hydroxy-3-methylglutaryl-CoA lyase, acetoacetyl-CoA 3-ketothiolase, propionyl-CoA carboxylase, methylmalonyl-CoA mutase, ATP:cobalamine adenosyltransferase, dihydrofolate reductase, methylenetetrahydrofolate reductase, cystathionine β-synthetase, the sarcosine dehydrogenase complex, proteins belonging to the system for cleaving glycine, β-alanine transaminase, serum carnosinase, cerebral homocarnosinase;

the genes associated with diseases of fat and fatty acid metabolism, such as for example lipoprotein lipase, apolipoprotein C-II, apolipoprotein E, other apolipoproteins, lecithin-cholesterol acyltransferase, LDL receptor, liver sterol hydroxylase, "phytanic acid" α-hydroxylase;

the genes associated with lysosomal deficiencies, such as for example lysosomal α-L-iduronidase, lysosomal iduronate sulphatase, lysosomal heparan N-sulphatase, lysosomal N-acetyl-α-D-glucosaminidase, lysosomal acetyl-CoA:α-glucosamine N-acetyltransferase, lysosomal N-acetyl-α-D-glucosamine 6-sulphatase, lysosomal galactosamine 6-sulphate sulphatase, lysosomal β-galactosidase, lysosomal arylsulphatase B, lysosomal β-glucuronidase, N-acetylglucosaminyl-phosphotransferase, lysosomal α-D-mannosidase, lysosomal α-neuraminidase, lysosomal aspartylglycosaminidase, lysosomal α-L-fucosidase, lysosomal acid lipase, lysosomal acid ceramidase, lysosomal sphingomyelinase, lysosomal glucocerebrosidase and lysosomal galactocerebrosidase, lysosomal galactosylceramidase, lysosomal arylsulphatase A, α-galactosidase A, lysosomal acid β-galactosidase, α chain of lysosomal hexoaminidase A.

There may also be mentioned, in a nonrestrictive manner, the genes associated with diseases of steroid and lipid metabolism, the genes associated with diseases of purine and pyrimidine metabolism, the genes associated with diseases of porphyrin and haem metabolism, the genes associated with diseases of connective tissue, and bone metabolism as well as the genes associated with blood diseases and diseases of the haematopoietic organs, muscle diseases (myopathy), diseases of the nervous system (neurodegenerative diseases) or diseases of the circulatory apparatus (treatment of ischaemias and of stenosis for example) and genes involved in mitochondrial genetic diseases.

In the method according to the invention, the nucleic acid may be combined with any type of vectors or any combination of these vectors which make it possible to improve the transfer of genes, for example, in a nonlimiting manner, with vectors such as viruses, synthetic or biosynthetic agents (for example lipid, polypeptide, glycosidic or polymeric agents), or beads which are propelled or otherwise. The nucleic acids may also be injected into a tissue which has been subjected to a treatment intended to improve the transfer of genes, for example a treatment of a pharmacological nature by local or systemic application, or an enzymatic, permeabilizing (use of surfactants), surgical, mechanical, thermal or physical treatment.

The advantage of the use of electrotransfer in gene therapy lies in the safety provided by the local treatment linked to the use of local and targeted electric fields.

By virtue of the safety linked to the use of weak fields, the present invention could be applied in the region of the cardiac muscle for the treatment of cardiopathies, for example using a suitable defibrillator. It could also be applied to the treatment of restenosis by the expression of genes inhibiting the proliferation of the smooth muscle cells such as the GAX protein.

The combination of fields which are not very intense and which are administered over long periods, applied to the tissues in vivo, improves the transfection of nucleic acids without causing notable damage to the tissues. These results improve the yield of DNA transfers within the context of gene therapy using nucleic acids.

Consequently, the method according to the invention makes it possible, for the first time, to envisage producing, by gene therapy, an agent at physiological and/or therapeutic doses, either in the tissues, or secreted in their vicinity or into the blood stream or the lymph circulation. Furthermore, the method according to the invention allows, for the first time, fine modulation and control of the effective quantity of transgene expressed by the possibility of modulating the volume of tissue to be transfected, for example with multiple sites of administration, or the possibility of modulating the number, the shape, the surface and the arrangement of the electrodes. An additional element of control comes from the possibility of modulating the efficiency of transfection by varying the field intensity, the number, the duration and the frequency of the pulses, and obviously according to the state of the art, the quantity and the volume of nucleic acids to be administered. It is thus possible to obtain an appropriate transfection level at the desired production or secretion level. The method finally allows increased safety compared with the chemical or viral methods for transferring genes in vivo, for which the affecting of organs other than the target organ cannot be completely excluded and controlled. Indeed, the method according to the invention allows control of the localization of the transfected tissues (strictly linked to the volume of tissue subjected to the local electrical pulses) and therefore provides the possibility of a return to the initial situation by complete or partial removal of the tissue when this is made possible by the non-vital character of this tissue and by its regeneration capacities as in the case of the liver or the muscle. This great flexibility of use makes it possible to optimize the method according to the animal species (human and veterinary applications), the age of the subject, his physiological and/or pathological condition.

The method according to the invention makes it possible, in addition, for the first time, to transfect nucleic acids of large size unlike the viral methods which are limited by the size of the capsid. This possibility is essential for the transfer of genes of a very large size such as that for dystrophin or genes with introns and/or regulatory elements of large size, which is necessary for example for a physiologically regulated production of hormones. This possibility is essential for the transfer of episomes or of yeast artificial chromosomes or of minichromosomes.

The following examples are intended to illustrate the invention in a nonlimiting manner.

In these examples, reference will be made to the following figures:

FIGS. 1a–1b: Effects of electrical pulses of high field intensity on the transfection of plasmid DNA pXL2774 into the cranial tibial muscle in mice; mean values±SEM, FIGS. 2a–2b: Effects of electrical pulses of intermediate field intensity on the transfection of plasmid DNA pXL2774 into the cranial tibial muscle in mice; mean values±SEM, FIGS. 3a–3b: Effects of electrical pulses of low field intensity and of different durations on the transfection of plasmid DNA pXL2774 into the cranial tibial muscle in mice; mean values±SEM, FIGS. 4a–4b: Effects of electrical pulses of low field intensity and of different durations on the transfection of plasmid DNA pXL2774 into the cranial tibial muscle in mice; mean values±SEM, FIG. 5: Efficiency of electrotransfection of plasmid DNA pXL2774 into the cranial tibial muscle of mice at low electric field intensities: mean values±SEM.

FIG. 6: Map of plasmids pXL3031 and pXL3010.

EXAMPLE 1

Experiment carried out under the conditions of the prior state of the art in which the electric fields prove to be inhibitors of transfection The standard electroporation conditions, such as those used in the prior art and which were discussed above, were tested and proved to be ineffective, or even to have an inhibitory action on the transfer of nucleic acids (plasmid DNA) into the striated muscle.

Materials and Methods—General Operating Conditions

In this example, the following products were used:

DNA pXL2774 (Patent PCT/FR 96/01414) is a plasmid DNA comprising the reporter gene for luciferase. Other products are available from commercial suppliers: Ketamine, Xylazine, physiological saline (0.9% NaCl).

An oscilloscope and a commercial generator of (rectangular or square) electrical pulses (electro-pulsator PS 15, Jouan, France) were used. The electrodes used are flat stainless steel electrodes 5.3 mm apart.

The experiment is carried out on the mouse C57 B1/6. Mice from different cages are randomly separated before the experiment ("randomization").

The mice are anaesthetized with a ketamine and xylazine mixture. The plasmid solution (30 $\mu$l of a solution at 500 $\mu$g/ml of 0.9% NaCl) is injected longitudinally through the skin into the cranial tibial muscle of the left and right legs with the aid of a Hamilton syringe. The two electrodes are coated with a conducting gel and the injected leg is placed between the electrodes in contact with them.

The electrical pulses are applied perpendicularly to the axis of the muscle with the aid of a generator of square pulses one minute after the injection. An oscilloscope makes it possible to control the intensity in volts (the values indicated in the examples represent the maximal values), the duration in milliseconds and the frequency in hertz of the pulses delivered, which is 1 Hz. 8 consecutive pulses are delivered.

To evaluate the transfection of the muscle, the mice are humanely killed 7 days after the administration of the plasmid. The cranial tibial muscles of the left and right legs are then removed, weighed, placed in lysis buffer and ground. The suspension obtained is centrifuged in order to obtain a clear supernatant. The measurement of the luciferase activity is carried out on 10 μl of supernatant with the aid of a commercial luminometer in which the substrate is added automatically to the solution. The intensity of the luminescent reaction is given in RLU (Relative Luminescence Unit) for a muscle knowing the total volume of suspension. Each experimental condition is tested on 10 points: 5 animals injected bilaterally. Statistical comparisons are carried out with the aid of non-parametric tests.

Results and Discussion

Two figures, of which the scale is linear or logarithmic, illustrate the results.

In this first experiment, the effects of an electric field of 800 to 1200 volts/cm which allows electroporation of tumours (Mir et al. Eur. J. Cancer 27, 68, 1991) were tested.

It is observed, according to FIG. 1, that relative to the control group, where the DNA is injected without an electrical pulse:

with 8 pulses of 1200 volts/cm and of a duration of 0.1 msec, the mean value of the luciferase activity is much lower, with pulses of 1200 volts/cm and of 1 msec, 3 animals are dead, the mean value of the luciferase activity is much lower, with pulses of 800 volts/cm and of 1 msec, the mean value of the luciferase activity is also significantly reduced.

Most of the muscles which were subjected to the action of the electric field are visibly impaired (friable and of a whitish appearance).

EXAMPLE 2

Experiment for electrotransfer of nucleic acids at moderate electric fields

This experiment is carried out with C57 B1/6 mice. Apart from the electric field intensity of the pulses and their duration, the practical conditions are those of Example 1.

Figure 2A:
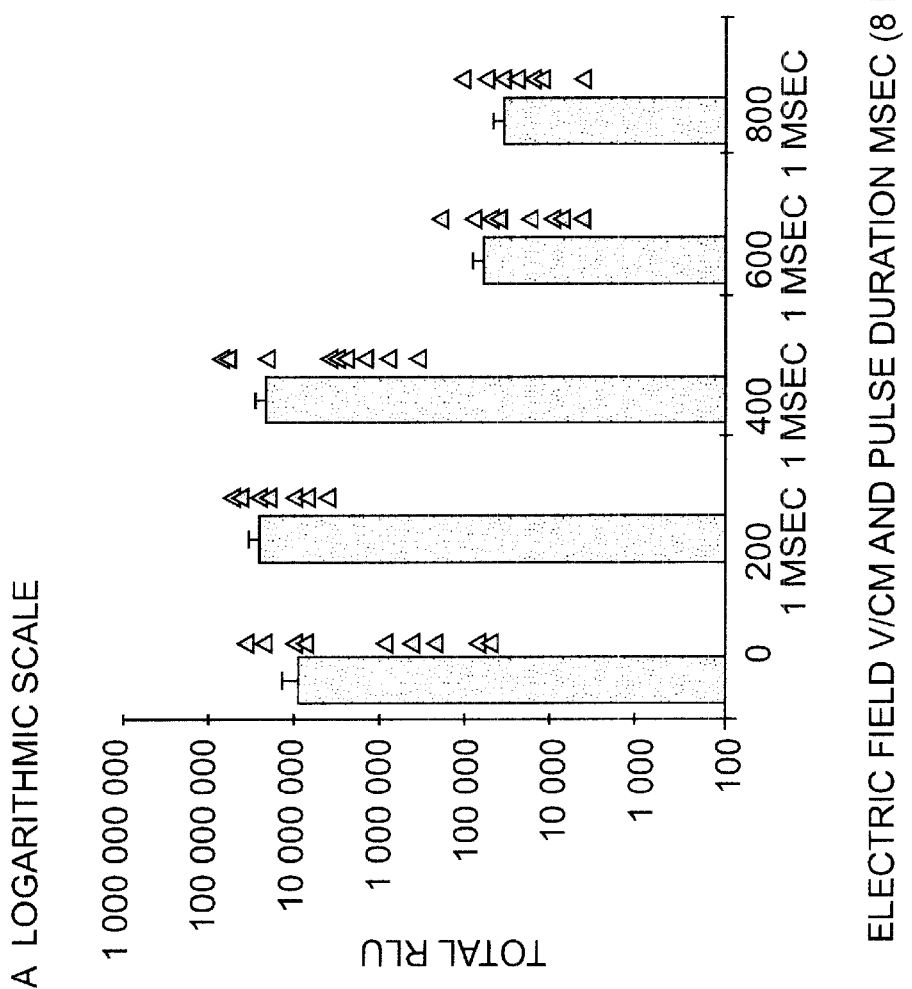
Figure 2B:
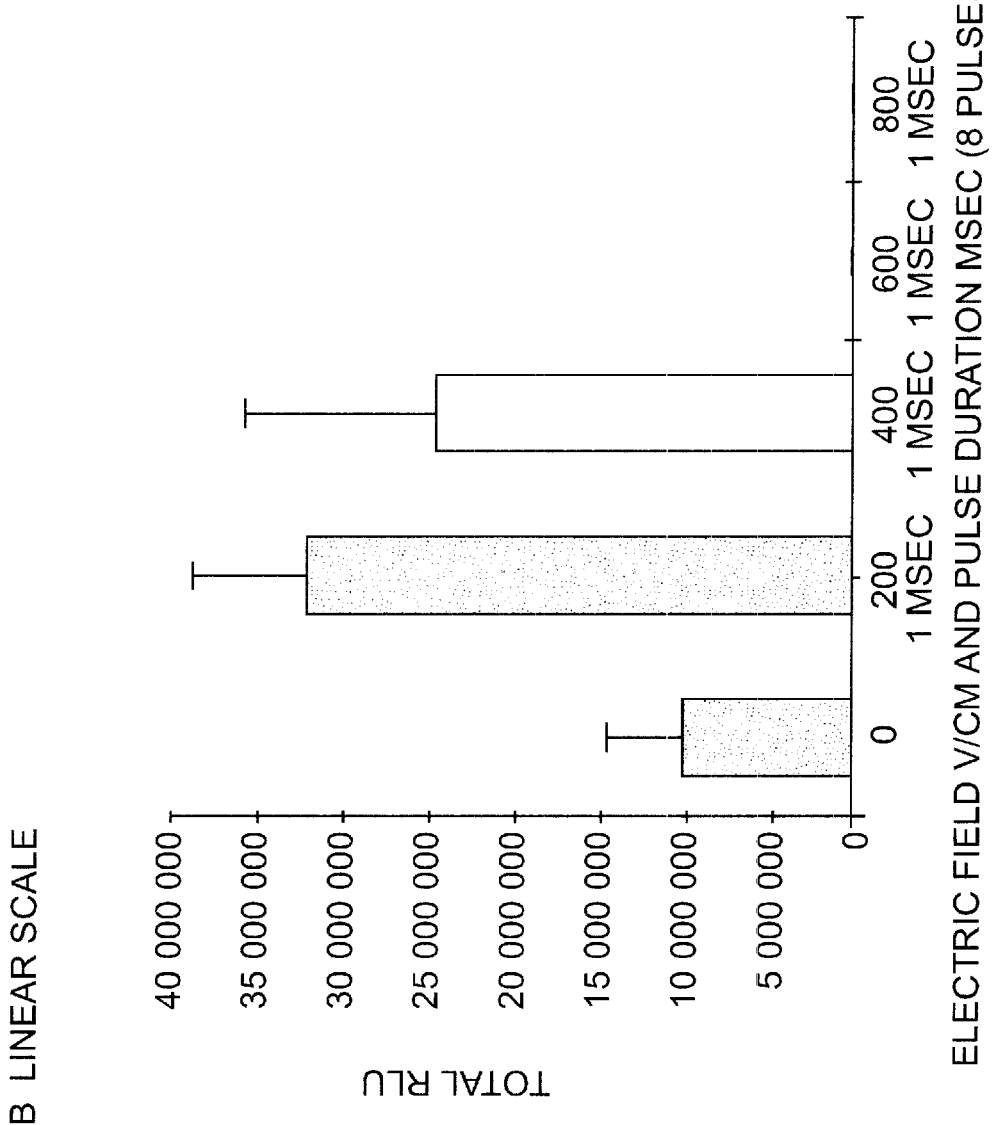

The results are shown in FIG. 2. The result of Example 1 is reproduced, that is to say the inhibitory effect of a series of 8 pulses at 800 volts/cm of a duration of 1 msec on the luciferase activity detected in the muscle. With a field of 600 volts/cm, the same inhibition and the same impairment of the muscle tissue are observed. On the other hand, in a remarkable and surprising manner, the decrease in voltage makes it possible to no longer visibly impair the muscles and, furthermore, at 400 and 200 volts/cm, the level of transfection of the muscles is on average greater than that obtained on the muscles not subjected to a field. It should be noted that, relative to the control group (not subjected to an electric field), the dispersion of the luciferase activity values is reduced at 200 volts/cm (SEM=20.59% of the mean value against 43.32% in the absence of electric field (FIG. 2A)).

EXAMPLE 3

Experiment for electrotransfer of nucleic acids with pulses of low field intensity showing a very high stimulation of the expression of the transgene This experiment is carried out with C57 B1/6 mice. Apart from the electric field intensity of the pulses and their duration, and the fact that the pulses are delivered 25 seconds after the injection of the DNA, the practical conditions are those of the preceding examples.

The results are shown in FIG. 3. The mean value of the expression of the luciferase transgene is markedly increased with a pulse duration of 20 msec at 100 volts/cm, and from a pulse duration of 5 msec at 200 volts/cm.

Figure 3A:
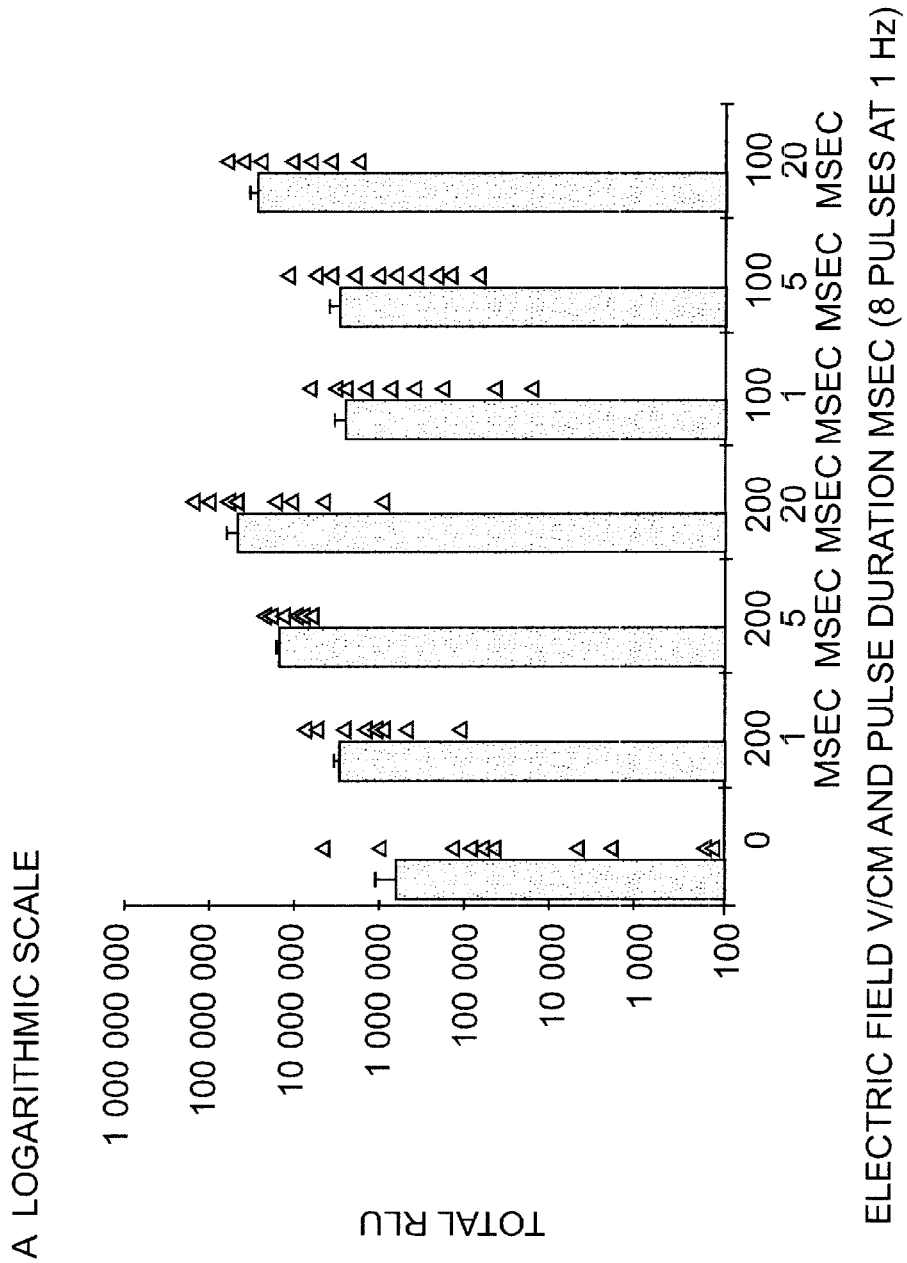
Figure 3B:
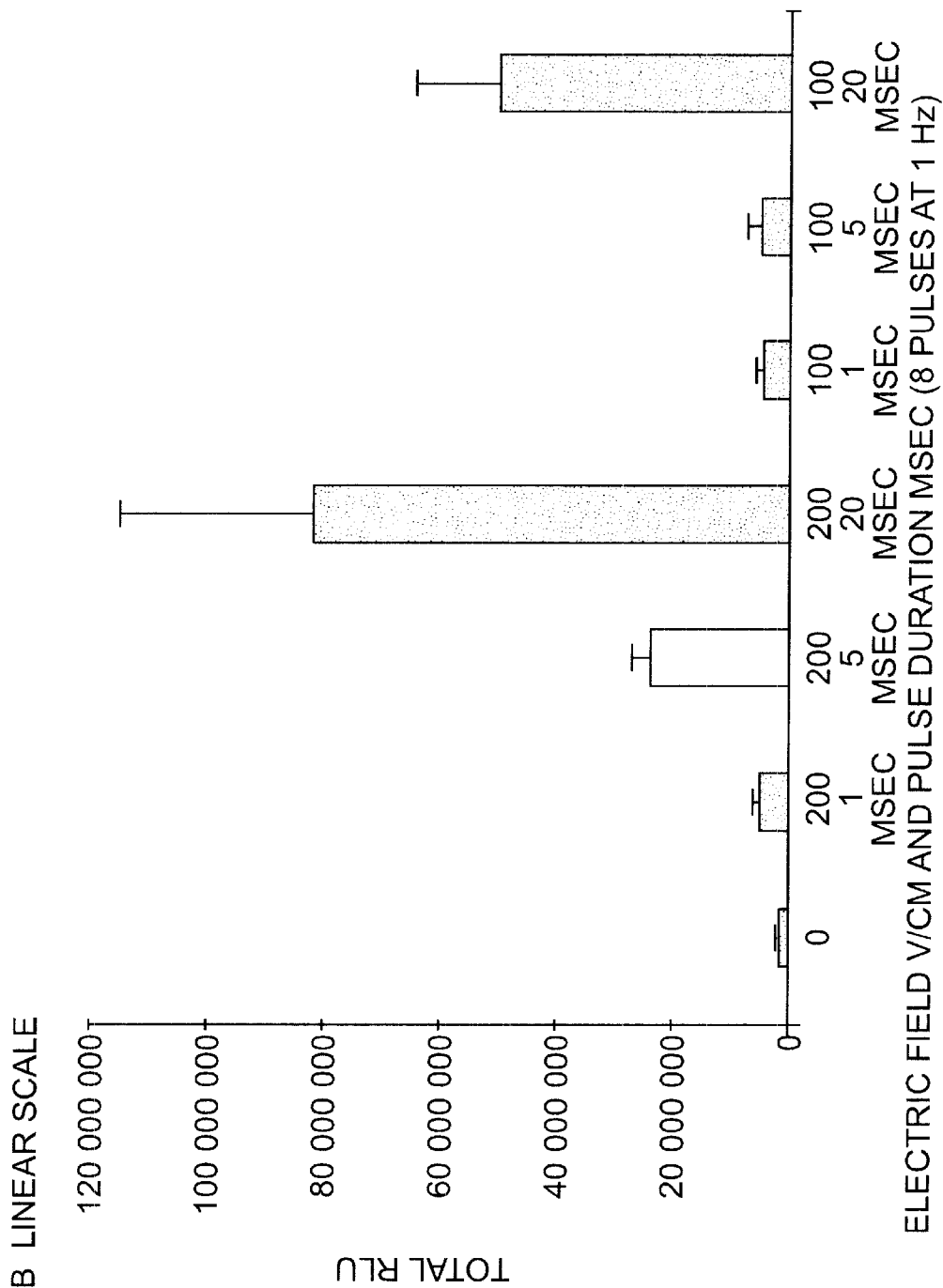
Figure 4A:
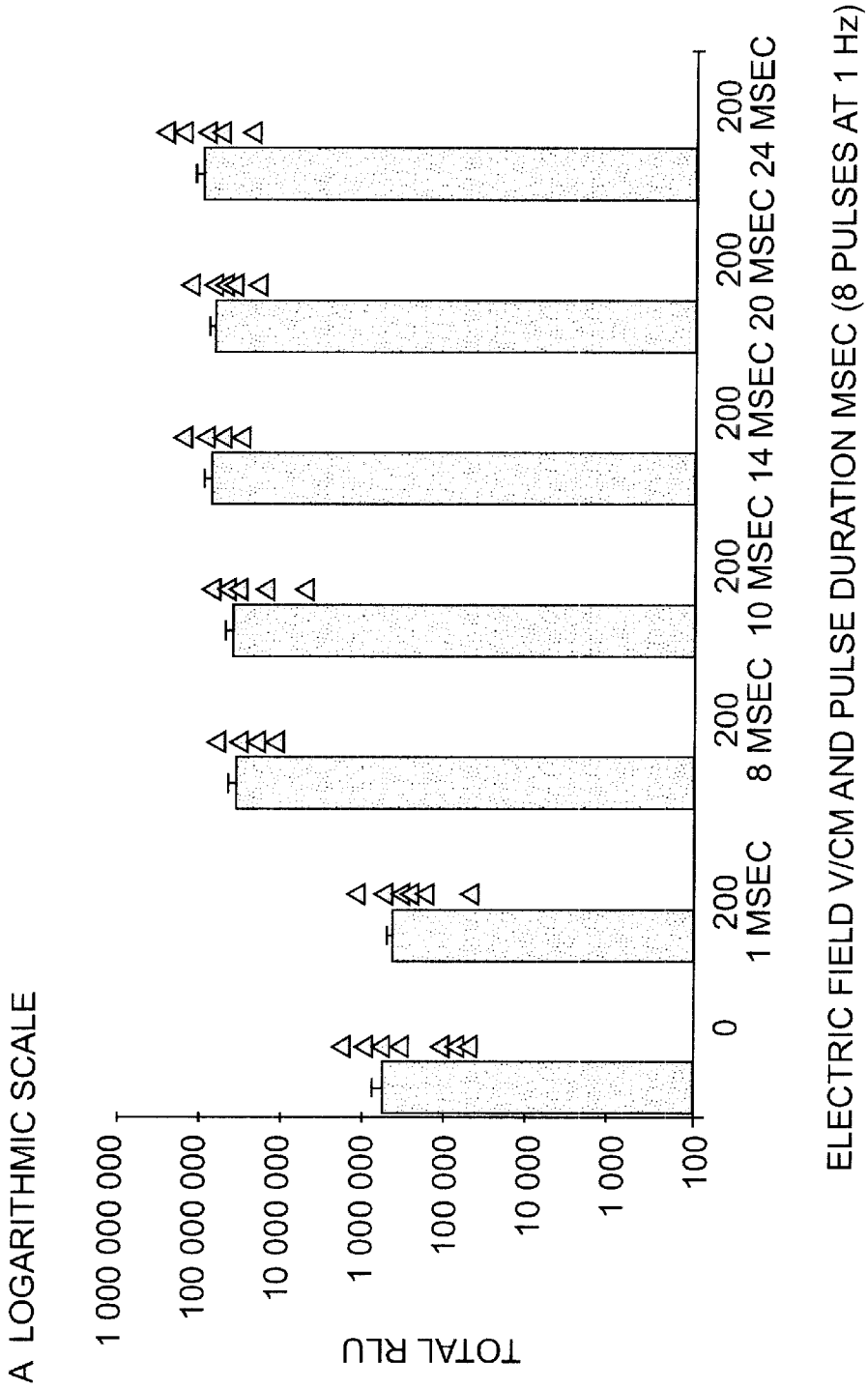
Figure 4B:
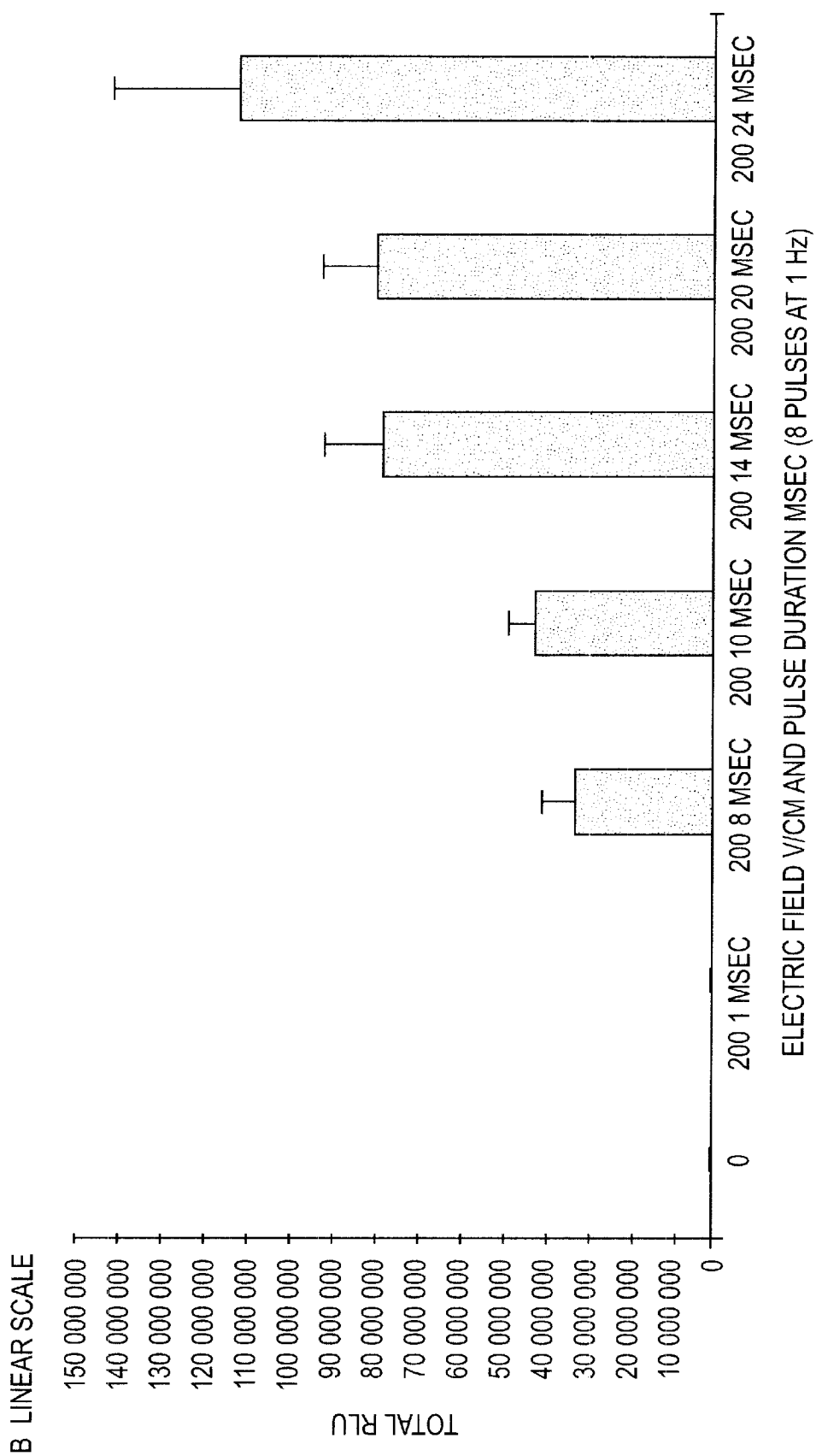

This experiment also clearly shows that the mean value of the luciferase activity obtained by electrotransfection of the DNA into the muscle is a function of the duration of the electrical pulses, when voltages of 200 and 100 volts/cm are used. It is also observed that the dispersion of the values is notably reduced for the electrotransfected muscle groups (FIG. 3A). In the absence of electrical pulses (control), the SEM represents 77.43% of the mean value whereas the relative SEM of the mean is reduced to 14% (200 volts/cm, 5 msec), 41.27% (200 volts/cm, 20 msec) and between 30% and 48% for the electrotransfer at 100 volts/cm of electric field.

Under the best condition for this experiment, the expression of the transgene is improved by a factor of 89.7 compared with the control injected in the absence of electrical pulses.

EXAMPLE 4

Experiment for electrotransfer of nucleic acids into the muscle at 200 volts/cm showing an increase in the expression of the transgene by a factor greater than 200

This experiment is carried out in DBA 2 mice, with electrical pulses of a field intensity of 200 volts/cm and of variable duration, the other conditions of this experiment being those of Example 3.

This example confirms that at 200 volts/cm, the transfection of the luciferase activity is increased from a pulse duration of 5 msec and then continues to increase for longer durations (FIGS. 4 and 5). Here again, a reduction in the inter-individual variability indicated by the SEM relative to the non-electrotransfected control (the relative value of the SEM is equal to 35% for the control and 25, 22, 16, 18, 16 and 26% for series of pulses of 1, 5, 10, 15, 20 and 24 msec respectively), is observed with electrotransfection.

Under the best condition for this experiment, the expression of the transgene is improved by a factor of 205 relative to the control injected in the absence of electrical pulses.

EXAMPLE 5

Efficiency of the electrotransfer of nucleic acids as a function of the product "number of pulses×field intensity×duration of each pulse"

FIG. 5 exemplifies the importance of the parameter corresponding to the product "number of pulses×field intensity×duration of each pulse". This parameter in fact corresponds to the integral, as a function of time, of the function which describes the variation of the electric field.

The representation in FIG. 5 of the results obtained during experiments 2, 3 and 4 with electric field intensities of 200 V/cm, 100 V/cm or in the absence of electric fields shows that the transfection efficiency increases as a function of the product of the total duration of exposure to the electric field by the field intensity. A stimulating effect is obtained for a value greater than 1 kV×msec/cm of the product "electric field×total duration of the pulses". According to a preferred mode, a stimulation is obtained for a value greater than or equal to 5 kV×msec/cm of the product "electric field×total duration of the pulses".

In the following examples, the electrotransfer of nucleic acids by means of the method according to the invention was tested on various tumours, either of human origin implanted on nude (immunodeficient) mice or of murine origin implanted on C57B1/6 (immunocompetent) mice.

EXAMPLE 6

Experiment for electrotransfer of nucleic acids into human pulmonary tumours H1299

The experiment is carried out in 18 to 20 g female nude mice. The mice are monolaterally implanted with grafts of H1299 tumours of 20 mm$^3$. The tumours develop, reaching a volume of 200 to 300 mm³. The mice are sorted according to the sizes of their tumours and divided into homogeneous groups. The mice are anaesthetized with a Ketamine, Xylazine mixture. The plasmid solution (40 μl of a solution at 250 μg/ml of DNA in 20 mM NaCl, 5% glucose) is longitudinally injected at the centre of the tumour with the aid of a Hamilton syringe. The side faces of the tumour are coated with conducting gel and the tumour is placed between the two electrodes. The electrodes are stainless steel plate electrodes 0.45 to 0.7 cm apart. An oscilloscope and a commercial generator of (rectangular or square) electrical pulses (electro-pulsator PS 15, Jouan, France) were used.

In this example, the plasmid used is plasmid pXL3031 (FIG. 6) containing the gene encoding luciferase (cytoplasmic). The plasmid pXL3031 is a vector derived from the vector pXL2774 (WO 97/10343) into which the luc+gene encoding modified *Photinus pyralis* luciferase (cytoplasmic) obtained from pGL3basic (Genbank: CVU47295) has been introduced under the control of the promoter obtained from the human cytomegalovirus early region (hCMV IE, Genbank HS5IEE) and the polyadenylation signal of the SV40 virus late region (Genbank SV4CG).

The electrical pulses are applied with the aid of a square pulse generator 20 to 30 sec after the injection. An oscilloscope makes it possible to control the intensity in Volts, the duration in milliseconds and the frequency in hertz of the pulses delivered, that is to say 200 to 800 Volts/cm, 20 msec and 1 hertz.

For the evaluation of tumour transfection, the mice (10 mice per condition) are humanely killed 2 days after the injection of the plasmid. The tumours are removed, weighed and ground in a lysis buffer. The suspension obtained is centrifuged in order to obtain a clear supernatant. The luciferase activity is measured in 10 μl of supernatant with the aid of a commercial luminometer in which the substrate is added automatically. The results are expressed in total RLU (Relative light Unit) per tumour.

In this example, two series of experiments were carried out in order to determine the effect of the electric field intensity on the efficiency of the transfection into the human pulmonary tumours H1299. In a first series of experiments, electric field intensities of 200 to 500 Volts/cm were tested. In a second series of experiments, electric field intensities varying from 400 to 800 Volts/cm were tested.

TABLE 1

Effect of electrical pulses of different field intensities on the transfection of plasmid DNA pXL 3031 on human tumors H1299 (non-small cell pulmonary carcinomas); mean values +/− SEM for the luciferase activity in RLU per tumour. Conditions: electric field intensity V/cm as indicated in the table, 8 pulses of 20 msec, frequency 1 Hertz.

|         | Experiment 1 |          | Experiment 2 |          |
|---------|--------------|----------|--------------|----------|
| Volt/cm | Mean         | SEM      | Mean         | SEM      |
| 0       | 32.8         | ±6.8     | 44.7         | ±10.2    |
| 200     | 129.7        | ±39.1    |              |          |
| 300     | 585.0        | ±134.8   |              |          |
| 400     | 5,266.6      | ±1,473.8 | 8,488.2      | ±3,881.7 |
| 500     |              |          | 14,201.6     | ±6,162.6 |
| 600     |              |          | 7,401.0      | ±5,323.1 |
| 800     |              |          | 11,884.1     | ±4,048.3 |

It is observed, according to Table 1, that relative to the control group where the DNA is injected without electrical pulse, the gene transfer is increased in a manner dependent on the electric field intensity of 200 to 400 Volts/cm to reach a plateau corresponding to the maximum transfection obtained from 500 volts/cm. At higher voltages (600 and 800 volts/cm), skin or deeper burns are obtained without, however, reducing the expression of the transgene.

The amplification of the gene transfer obtained by electrotransfer into the pulmonary tumours H1299 is of the order of 240 to 320 fold.

EXAMPLE 7

Experiment for electrotransfer of nucleic acids into human colon tumours HT29

The experiment is carried out in 18 to 20 g female nude mice. The mice are monolaterally implanted with grafts of tumours HT29 of 20 mm³. The tumours develop, reaching a volume of 100 to 200 mm³. The mice are sorted according to the size of their tumours and divided into homogeneous groups. Apart from the distance used between the electrodes (0.45 cm), the implementation conditions are those of Example 6. The results of two series of independent experiments are presented in Table 2.

TABLE 2

Effect of electrical pulses of different field intensities on the transfection of plasmid DNA pXL 3031 on human tumours HT29 (colon adenocarcinomas); mean values +/− SEM for the luciferase activity in RLU per tumour. Conditions: electric field intensity V/cm as indicated in the table, 8 pulses of 20 msec, frequency 1 Hertz.

|         | Experiment 1 |      | Experiment 2 |      |
|---------|--------------|------|--------------|------|
| Volt/cm | Mean         | SEM  | Mean         | SEM  |
| 0       | 4.0          | ±1.8 | 0.6          | ±0.3 |
| 400     | 16.0         | ±5.4 |              |      |
| 500     | 14.1         | ±7.6 | 5.5          | ±3.6 |
| 600     | 24.2         | ±9.2 | 14.6         | ±6.4 |

Compared with the control groups without electrotransfer, the application of an electric field of an intensity of 600 volts/cm makes it possible to reach an optimum level of transfection regardless of the base level of transfection without electrotransfer. The improvement in the transfection is by a factor of 6 to 23 fold respectively, and is relatively similar from 400 to 600 Volts/cm.

EXAMPLE 8

Experiment for electrotransfer of nucleic acids into murine fibrosarcomas

The experiment is carried out in 18 to 20 g C57B1/6 mice. The mice are monolaterally implanted with 1×10⁶ LPB cells in 100 μl of serum-free MEM medium. The tumours develop, reaching a volume of 100 to 200 mm³. The mice are sorted according to the size of their tumours and divided into homogeneous groups. The conditions for carrying out the experiment are those of Example 6.

The results of two series of independent experiments are presented in Table 3.

TABLE 3

Effect of electrical pulses of different field
intensities on the transfection of plasmid DNA pXL 3031
on murine fibrosarcomas; mean values +/− SEM for the
luciferase activity in RLU per tumour. Conditions:
electric field intensity V/cm as indicated in the
table, 8 pulses of 20 msec, frequency 1 Hertz.

| | Experiment 1 | | Experiment 2 | |
|---|---|---|---|---|
| Volt/cm | Mean | SEM | Mean | SEM |
| 0 | 0.6 | ±0.3 | 0.4 | ±0.1 |
| 300 | 26.3 | ±14.8 | 11.6 | ±4.6 |
| 400 | 42.5 | ±31.2 | 10.4 | ±3.5 |
| 500 | 17.0 | ±12.8 | 6.0 | ±1.8 |
| 600 | | | 11.0 | ±7.1 |

Compared with the control groups without electrotransfer, the application of an electric field of an intensity of 300 to 600 Volts/cm makes it possible to improve the gene transfer by a factor of 30 to 70, regardless of the applied voltage.

EXAMPLE 9

Experiment for electrotransfer of nucleic acids into murine B16 melanomas

The experiment is carried out in 18 to 20 g C57B1/6 mice. The mice are monolaterally implanted with grafts of B16 tumours of 20 mm³. The tumours develop, reaching a volume of 200 to 300 mm³. The mice are sorted according to the size of their tumours and divided into homogeneous groups.

The conditions for carrying out the experiment are those of Example 6.

The results are presented in Table 4.

TABLE 4

Effect of electrical pulses of different field
intensities on the transfection of plasmid DNA pXL 3031
murine B16 melanomas; mean values +/− SEM for the
luciferase activity in RLU per tumour. Conditions:
electric field intensity V/cm as indicated in the
table, 8 pulses of 20 msec, frequency 1 Hertz.

| | Experiment 1 | |
|---|---|---|
| Volt/cm | Mean | SEM |
| 0 | 1.3 | ±0.7 |
| 300 | 14.3 | ±7.6 |
| 500 | 32.2 | ±12.6 |
| 600 | 17.2 | ±6.2 |

Compared with the control group without electrotransfer, the application of an electrical field of an intensity of 500 Volts/cm makes it possible to improve the gene transfer by a factor of 24.

EXAMPLE 10

Experiment for electrotransfer of nucleic acids into murine 3LL tumours

The experiment is carried out in 18 to 20 g C57B1/6 mice. The mice are monolaterally implanted with grafts of 3LL tumours of 20 mm³.

The size of the transfected tumours obtained five days after the implantation is 30 mm³. The conditions for carrying out the experiment are those of Example 6. The results are presented in Table 5.

TABLE 5

Effect of electrical pulses of different field
intensities on the transfection of plasmid DNA pXL 3031
on murine 3LL pulmonary carcinomas; mean values +/− SEM
for the luciferase activity in RLU per tumour.
Conditions: electric field intensity V/cm as indicated
in the table, 8 pulses of 20 msec, frequency 1 Hertz.

| Volt/cm | Mean | SEM |
|---|---|---|
| 0 | 0.1 | ±0.04 |
| 300 | 3.7 | ±2.9 |
| 500 | 470.5 | ±237.6 |
| 600 | 53.3 | ±23.9 |

The application of an electric field of an intensity of 500 Volts/cm makes it possible to increase the expression of the transgene by a factor of 3885.

These remarkable results should be related to the fact that these tumours are only very slightly transfectable with DNA when the DNA is simply injected without electrotransfer.

EXAMPLE 11

Experiment for electrotransfer of nucleic acids into human pulmonary tumours H1299, effect on the secretion into the plasma of the secreted human alkaline phosphatase.

In this example, the DNA pXL3010 (FIG. 6) used is a plasmid DNA containing the gene encoding the secreted placental human alkaline phosphatase.

The plasmid pXL3010 is a vector derived from ColE1 into which the gene encoding the secreted alkaline phosphatase obtained from pSEAP-basic (Clontech, Genbank: CVU09660) has been introduced under the control of the CMV promoter obtained from the plasmid pCDNA3 (Invitrogen, the Netherlands) and of the polyadenylation signal of the SV40 virus late region (Genbank SV4CG).

The experiment is carried out in 18 to 20 g nude mice. The mice are monolaterally implanted with grafts of H1299 tumours of 20 mm³. The tumours develop, reaching a volume of 200 to 300 mm³. The mice are sorted according to the size of their tumours and divided into homogeneous groups.

The tumours are transfected under the implementation conditions of Example 6 with, however, a single voltage condition, that is to say 500 Volts/cm, 20 msec and 1 hertz.

The assays of alkaline phosphatase are carried out in the plasma with the aid of the Phospha-light kit (Tropix) on day D1, D2 and D8 after the transfection with or without electrotransfer. The results are presented in Table 6.

TABLE 6

Effect of electrical pulses of different field
intensities on the secretion of an exogeneous protein:
human alkaline phosphatase secreted following
transfection of plasmid DNA pXL 3010 in human tumours
H1299; mean values +/− SEM for the alkaline phosphatase
(ng/ml). Conditions: electrical field intensity V/cm as
indicated in the table, 8 pulses of 20 msec, frequency 1 Hertz.

| | Alkaline phosphatase in the plasma | |
|---|---|---|
| Sample collection | 0 Volt/cm (MOY +/− SEM) | 500 Volts/cm (MOY +/− SEM) |
| D1 | 1.42 ± 0.07 | 8.90 ± 1.74 |
| D2 | 1.40 ± 0.01 | 9.04 ± 1.55 |
| D8 | 1.31 ± 0.01 | 1.67 ± 0.12 |

All the results presented in Examples 6 to 11 show that the electrotransfer of nucleic acids under the conditions of the method according to the invention makes it possible to remarkably increase the level of expression of the transgene, in various types of tumours. Furthermore, in the case of transgene encoding a secreted protein, the intratumour administration of the plasmid by electrotransfer makes it possible to significantly increase the plasma concentration of the secreted protein.

EXAMPLE 12
Effect of the increase of the duration of the electrical pulses

This example illustrates that it is possible to increase the unit duration of the pulses well above the values tested in Example 4.

This experiment is carried out with C57B1/6 mice. The plasmid used is the plasmid pXL2774, the quantity of DNA administered is 15 μg. The electropulsator used to deliver the electrical pulses of a duration greater than 20 msec is a commercial electropulsator (Genetronics, model T 820, USA, San Diego, Calif.). The electrical pulses are variable in number and duration but have a constant field intensity of 200 Volts/cm; the other conditions for this experiment are those described in Example 1. The results are presented in Table 7.

TABLE 8

Mean value +/− SEM for the luciferase activity in millions RLU per muscle. N = 10 per group. Conditions: field intensity 200 V/cm, variable number of pulses of 20 msec, frequency 1 Hz.

| Number of pulses | 0 | 1 | 2 | 4 | 6 | 8 | 12 | 16 |
|---|---|---|---|---|---|---|---|---|
| Total RLU | 70 ± 56 | 147 ± 26 | 281 ± 46 | 439 ± 50 | 678 ± 129 | 819 ± 73 | 929 ± 169 | 890 ± 137 |

It is observed that the expression of the luciferase increases substantially from the application of a single pulse, and that it continues to increase as a function of the number of pulses. It thus appears that the variation of the number of pulses delivered is a means of modulating the efficiency of the transfer of nucleic acids and of adjusting the level of expression of the transgene.

The reduction in the variability of the response demonstrated by the reduction in the value of the SEM relative to

TABLE 7

Mean values +/− SEM for the luciferase activity in millions of RLU per muscle. N = 10 for each group.
Electrotransfer conditions: field intensity 200 V/cm, 8 or 4 pulses (variable unit duration), frequency 1 Hz.

| Pulse duration (msec) | 0 | 1 | 5 | 10 | 20 | 30 | 40 | 50 | 60 | 80 |
|---|---|---|---|---|---|---|---|---|---|---|
| Experiment A 8 pulses | 11 ± 5 | 39 ± 6 | 211 ± 26 | 288 ± 46 | 1158 ± 238 | 1487 ± 421 | 2386 ± 278 | | | |
| Experiment A 4 pulses | 11 ± 5 | 26.8 ± 6 | 123 ± 17 | 246 ± 32 | 575 ± 88 | 704 ± 130 | | 3440 ± 1077 | | |
| Experiment B 4 pulse | 15 ± 8 | | | | | | | 2885 ± 644 | 2626 ± 441 | 1258 ± 309 |

An increase in the expression of the transgene is observed with the extension of the unit duration of the pulses (at least up to 40 msec for a series of 8 pulses and at least up to 50 msec for a series of 4 pulses of an intensity of 200 Volts/cm). This example shows that the optimum duration of the pulses depends on the number of pulses used and that the unit duration of the pulses may reach at least 80 msec, this value for the duration not being limiting.

EXAMPLE 13
Efficiency of electrotransfer as a function of the number of electrical pulses This example demonstrates the effect of the increase in the number of electrical pulses on the efficiency of the transfer of nucleic acids.

This experiment is carried out with C57B1/6 mice. The plasmid used is the plasmid pXL 2774, the quantity of DNA administered is 15 μg. The electrical pulses are variable in number. The duration of each pulse is 20 msec. The field intensity is 200 Volts/cm. The other conditions for this experiment are those described in Example 1. The results are presented in Table 8.

the mean for all the groups subjected to the electrotransfer is also confirmed.

EXAMPLE 14
Effect of the increase in the frequency of the electrical pulses.

This example shows that the increase in the frequency of the pulses unexpectedly makes it possible to improve the efficiency of the transfection. Moreover, and in a clinical perspective, the increase in the frequency must improve the comfort of the patient by reducing the total duration of the treatment.

This experiment is carried out with C57B1/6 mice. The plasmid used is the plasmid pXL 2774, the quantity of DNA administered is 15 μg. The frequency of the electrical pulses is variable (from 0.1 to 4 Hertz). The duration of each pulse is 20 msec, the field intensity is 200 Volts/cm, the other conditions for this experiment are those described in Example 1. The results are presented in Table 9.

TABLE 9

Mean values +/− SEM for the luciferase activity in millions of RLU per muscle. N = 10 for each group. Conditions: field intensity 200 V/cm, 8 or 4 pulses of 20 msec, variable frequency.

| Frequency Hertz | 0 | 0.1 | 0.2 | 0.5 | 1 | 2 | 3 | 4 |
|---|---|---|---|---|---|---|---|---|
| Experiment A 8 pulses | 5 ± 2 | 54 ± 13 | 95 ± 16 | 405 ± 60 | 996 ± 156 | 1528 ± 257 | | |
| Experiment A 4 pulses | | 114 ± 14 | 163 ± 24 | 175 ± 26 | 337 ± 53 | 587 ± 90 | | |
| Experiment B 8 pulses | 21 ± 14 | | | | 1294 ± 189 | 2141 ± 387 | 3634 ± 868 | 2819 ± 493 |
| Experiment B 4 pulses | | | | | 1451 ± 228 | 1572 ± 320 | 1222 ± 126 | 2474 ± 646 |

The results obtained in experiment "A", Table 9 show that the highest frequencies ($\geq 1$ Hz) are more effective than the lower frequencies which correspond to a longer duration between two consecutive pulses (10 seconds at 0.1 Hertz). The transfection efficiency increases with the frequency over the range of values tested from 0.1 to 4 Hertz for 4 pulses and from 0.1 to 3 Hertz for 8 pulses.

EXAMPLE 15

Effect of the application of an electric field varying according to a decreasing exponential as a function of time.

This example demonstrates the effect of the application of an electric field varying according to a decreasing exponential on the efficiency of the transfer of nucleic acids.

This experiment is carried out with C57B1/6 mice.

The plasmid used is the plasmid pXL 3031. The plasmid pXL3031 (FIG. 12) is a vector derived from the plasmid pXL2774 (WO 97/10343) into which the luc+gene encoding the modified *Photinus pyralis* luciferase (cytoplasmic) obtained from pGL3basic (Genbank: CVU47295) has been introduced under the ocntrol of a promoter obtained from the human cytomegalovirus early region (hCMV IE, Genbank HS5IEE) and of the polyadenylation signal of the SV40 virus late region (Genbank SV4CG). The quantity of DNA administered is 10 µg.

The electrical pulse generator used makes it possible to deliver pulses of an electric field intensity varying according to a decreasing exponential as a function of time (Equibio electropulsator, model easyjectT plus, Kent UK). The voltage imposed is the exponential peak voltage. The second adjustable parameter is the capacitance (µFarads) which makes it possible to vary the quantity of energy delivered and the exponential time constant. The results are presented in Table 10.

TABLE 10

Factor of increase in expression (luciferase activity) obtained by application of an exponentially decreasing pulse. The increase factor is calculated with reference to the luciferase activity obtained with the administration of the plasmid pXL3031 without electrotransfer. (Mean values of the increase factor, N = 4 to 6 per condition).

| | Capa µF 150 | Capa µF 300 | Capa µF 450 | Capa µF 600 | Capa µF 1200 | Capa µF 2400 | Capa µF 3000 |
|---|---|---|---|---|---|---|---|
| 40 V/cm | | | | | | 1.23 | 11 |
| 100 V/cm | | | | 16.5 | 2.8 | 6.5 | 23.9 |
| 150 V/cm | | | | 1.8 | 3.5 | 6.1 | |
| 200 V/cm | | 5.1 | | 15.8 | 18.8 | 121.5 | 189.7 |
| 300 V/cm | 32.1 | 90.5 | 48.7 | 760.4 | 56.2 | | |
| 400 V/cm | | 795 | | | | | |

TABLE 10-continued

Factor of increase in expression (luciferase activity) obtained by application of an exponentially decreasing pulse. The increase factor is calculated with reference to the luciferase activity obtained with the administration of the plasmid pXL3031 without electrotransfer. (Mean values of the increase factor, N = 4 to 6 per condition).

| | Capa µF 150 | Capa µF 300 | Capa µF 450 | Capa µF 600 | Capa µF 1200 | Capa µF 2400 | Capa µF 3000 |
|---|---|---|---|---|---|---|---|
| 600 V/cm | 62 | | | | | | |
| 800 V/cm | 3.1 | 1.1 | | | | | |

By way of comparison, the factor of increase in expression obtained for the transfer of pXL3031 in the presence of an electric field with square-shaped pulses (field intensity of 200 V/cm, 8 pulses of 20 msec, at a frequency of 1 Hertz) was 44 in the same experiment.

These results show that it is possible to use electrical pulses of square shape or of exponentially decreasing intensity as a function of time. Furthermore, in the latter case, a substantial increase in expression may be obtained for a low field value and a high capacitance (e.g. 200 V/cm, capacitance 3000 µFarad) or a high field value and a low capacitance (e.g. 400 V/cm, capacitance 300 µFarad).

EXAMPLE 16

Effect of the combination of a brief pulse of high voltage and of several long pulses of low voltage.

This example shows that the electric field delivered may be a combination of at least one field between 500 and 800 Volta/cm for a short duration, for example 50 or 100 µsec, and of at least one weak field (<100 Volts/cm) for a longer duration, for example $\geq 1$ msec and up to 90 msec in this experiment.

The low electric field values here are 80 V/cm applied at 4 pulses of a duration of 90 msec with a frequency of 1 Hertz. For this experiment, two electropulsators are used. The electrical pulses are applied by one and then the other apparatus, the change being made in less than one second with the aid of a manual control.

The plasmid used is the plasmid pXL3031. The quantity of DNA administered is 3 µg. The electric field values are indicated in Table 11; the other conditions for this experiment are those described in Example 1.

TABLE 11

Mean values +/− SEM for the
luciferase activity in millions of RLU per muscle.
N = 10 muscles per group.

| Conditions for application of the electric field | Experiment 1 (3 μg pXL3031) | Experiment 2 (3 μg pXL3031) |
|---|---|---|
| Control (absence of electric field) | 320 +/− 126 | 75 +/− 27 |
| A1: 500 V/cm, 1 × 0.1 msec | — | 169 +/− 63 |
| A3: 800 V/cm, 1 × 0.1 msec | 416 +/− 143 | 272 +/− 84 |
| B: 80 V/cm, 4 × 90 msec | 1282 +/− 203 | 362.21 +/− 85.17 |
| Conditions A1 then B | — | 1479 +/− 276 |
| Conditions A3 then B | 3991 +/− 418 | 1426 +/− 209 |
| Conditions B then A3 | — | 347 +/− 66 |

Table 11, summarizing the results obtained for two series of experiments, shows that a brief pulse of high voltage or that four successive long pulses of low voltage only slightly improve the transfection compared with the control group which received an injection of pXL3031 but was not subjected to an electric field. The same applies when the low field pulses are applied before the high field pulse.

On the other hand, in the two series of experiments, the combination of a brief pulse of high voltage followed by four successive long pulses of low voltage very considerably increases the efficiency of the transfer of the DNA.

The results obtained in Examples 1 and 2 showed that 8 pulses of 600, 800 or 1200 volts of a unit duration of 1 msec at 1 Hz caused lesions and inhibited transfection. The results obtained in Example 16 show that, under particular conditions, it is possible to use high voltage field intensities in a manner which does not cause lesions; indeed, from a macroscopic point of view, the muscles are never visibly impaired. The use of high electric fields of brief duration combined with low fields of longer duration appears as an additional means of modulating the efficiency of the transfer of the DNA.

EXAMPLE 17

Effect of the time of injection of the nucleic acid relative to the application of the electric field.

This example illustrates the fact that the nucleic acid may be administered at least 30 minutes, and even at least one hour, before the application of the electric field.

This experiment is carried out with C57B1/6 mice. The plasmid used is the plasmid pXL 2774. The quantity of DNA administered is 15 μg or 1.5 μg. The injection of DNA is followed, or preceded, by the application of an electric field under the following conditions: intensity 200 V/cm, 8 pulses of 20 msec, frequency 1 Hz. The other conditions for this experiment are those described in Example 1. A control group consists of animals which received an injection of the plasmid but were not subjected to the electrical pulses. The results are presented in Table 12.

TABLE 12

Mean values +/− SEM for the
luciferase activity in millions of RLU per muscle.
N = 10 muscles per group.

Table 12A: Injection of DNA in the absence of electric field

| | Exp 1 pXL2774 (15 μg) | Exp 2 pXL 2774 (15 μg) | Exp 3 pXL 2774 (1.5 μg) | Exp 4 pXL 2774 (15 μg) | Exp 5 pXL 2774 (1.5 μg) |
|---|---|---|---|---|---|
| Control | 7 ± 4 | 8 ± 6 | 0.4 ± 0.2 | 22 ± 15 | 1 ± 1 |

Table 12B: Injection of DNA before application of the electric field

| time | Exp 1 | Exp 2 | Exp 3 | Exp 4 | Exp 5 |
|---|---|---|---|---|---|
| −120 min | | | | 20 ± 5 | 1 ± 1 |
| −60 min | | | | 106 ± 22 | 10 ± 3 |
| −30 min | 303 ± 36 | 237 ± 61 | 7 ± 3 | 184 ± 22 | 15 ± 4 |
| −5 min | 410 ± 7 | | | | |
| −60 sec | 253 ± 51 | | | | |
| −20 sec | 492 ± 122 | 201 ± 43 | 9 ± 3 | 123 ± 23 | 12 ± 2 |

Table 12C: Injection of DNA after application of the electric field

| time | Exp 1 | Exp 2 | Exp 3 | Exp 4 | Exp 5 |
|---|---|---|---|---|---|
| +10 sec | | | | 7 ± 7 | |
| +20 sec | 11 ± 6 | 0.4 ± 0.1 | | | |
| +60 sec | 8 ± 7 | | | 17 ± 15 | |

The presence of the DNA at the time of the application of the electric field is a condition for the efficiency of the electrotransfection. Remarkably, it is observed that the injection of the plasmid may be carried out at least 30 minutes and even 1 hour (Experiments 4 and 5) before the application of the electric field, without notably modifying the level of expression. A similar result is obtained both with with a dose of 15 μg of plasmid per muscle and with a 10-fold lower dose of 1.5 μg.

These observations make it possible in particular to envisage multiple injections, at variable times, of the same plasmid, or of different plasmids into the muscle prior to the application of the electric field. It is also possible to make multiple injections over an extended region of the muscle and then to apply a series of electrical pulses over the entire injected territory to be treated.

EXAMPLE 18

Transfer of a gene encoding erythropoietin (EPO)

Adult C57B1/6 mice received, in the cranial tibial muscle and unilaterally, an injection of plasmid pXL3348. The plasmid pXL3348 (FIG. 16) is a vector derived from the plasmid pXL2774 into which the murine gene for erythropoietin (NCBI: 193086) has been introduced under the control of the promoter obtained from the human cytomegalovirus early region (hCMV IE) and of the polyadenylation signal of the SV40 virus late region (Genbank SV4CG).

The conditions for electrotransfer are the following: electric field intensity 200 V/cm, 8 pulses of 20 msec, frequency 1 Hz. The electric field is applied imemdiately after injection of the plasmid DNA.

TABLE 13

Mean values ± SEM. N = 4 to 5.

| Plasmid | Serum erythropoietin (mIU/ml) at D7 | | Serum erythropoietin (mIU/ml) at D24 | |
|---|---|---|---|---|
| | Electro-transfer − | Electro-transfer + | Electro-transfer − | Electro-transfer + |
| pXL3348 (1 μg) | 0 | 3.0 ± 1.6 | 0 | 1.12 ± 0.8 |
| pXL3348 (10 μg) | 0.9 ± 0.9 | 61.8 ± 15.8 | 0 | 74.1 ± 28.9 |
| pUCl9 (1 μg) | | 0 | | 0 |

| Plasmid | Haematocrit % sample collection at D7 | | Haematocrit % Sample collection at D24 | |
|---|---|---|---|---|
| | Electro-transfer − | Electro-transfer + | Electro-transfer − | Electro-transfer + |
| pXL3348 (1 μg) | 38.5 ± 0.5 | 35.0 ± 3.6 | 50.8 ± 2.3 | 81 ± 0.5 |
| pXL3348 (10 μg) | 32.0 ± 3.2 | 26.0 ± 4.1 | 69.0 ± 5.1 | 83.0 ± 1.0 |
| PUC 19 (1 μg) | | 30.8 ± 2.3 | | 43.2 ± 0.9 |

With electrotransfer, a very clear increase in the quantity of erythropoietin in the blood at D7 and D24 is observed for the administration of 10 μg of pXL3348. Furthermore, the physiological effect of the increase in erythropoietin which results in an increase in the haematocrit is very high (85%), from D7, even for a very small quantity of plasmid (1 μg).

EXAMPLE 19

Effect of the electrotransfer on the expression of vaccinal transgenes

This example demonstrates that the method according to the invention is also applicable to the transfer of genes encoding polypeptides of vaccinal importance.

The experiment is carried out in 9-week old female Balb/c mice. The electrodes used are stainless steel plate electrodes 5 mm apart. VR-HA is a plasmid DNA containing the haemagglutinin gene of the influenza virus (strain A/PR/8/34). VR-gB is a plasmid DNA containing the gene for glycoprotein B (gB) of the human cytomegalovirus (Towne strain).

The plasmid solution (50 μl of a solution at 20 μg/ml or 200 μ/ml in 0.9% NaCl) is longitudinally injected through the skin into the cranial tibial muscle unilaterally. The electrical pulses are applied 20 sec after the administration of the plasmid, perpendicularly to the axis of the muscle with the aid of the square pulse generator (electric field intensity 200 V/cm, 8 consecutive pulses of a duration of 20 msec, frequency 1 Hz).

For the evaluation of the stimulation of the immune response, the following immunization protocol was followed:

| D 0 | collection of the preimmune serum |
|---|---|
| D 1 | primary injection, plus or minus electrotransfer |
| D 2 | collection of the immune serum |
| D 2 | injection of booster, plus or minus electrotransfer |
| D 42 | Collection of immune serum |
| D 63 | collection of immune serum |

The blood samples are collected at the level of the retro-orbital sinus. The assays of the specific antibodies are carried out by ELISA. Each experimental condition is tested on 10 animals injected unilaterally.

The results relating to the titres of antibodies directed against the influenza virus haemagglutinin are presented in Table 14 A.

TABLE 14-a

Titres of antibodies directed against the influenza virus haemaglutinin, obtained after injection of 1 or 10 μg of DNA (VR-HA) in the absence or in the presence of electrical pulses. The results are the geometric means for 10 animals (8 animals for the group injected with 1 μg of DNA in the presence of electrical pulses and samples collected at D63) ± standard deviation. The value of p was obtained by comparing in pairs the groups injected in the presence and in the absence of electrical pulses using the Man-Whitney nonparametric test.

| | Electro-transfer | D0 | D21 | D42 | D63 |
|---|---|---|---|---|---|
| VR-HA (1 μg) | − | <50 | 132 ± 739 | 1201 ± 4380 | 1314 ± 2481 |
| VR-HA (1 μg) (p) | + | <50 | 1121 ± 1237 (0.0135) | 10441 ± 7819 (0.0022) | 8121 ± 5619 (0.0033) |
| VR-HA (10 μG) | − | <50 | 781 ± 666 | 5113 ± 16015 | 4673 ± 8238 |
| VR-HA (10 μG) (p) | + | <50 | 4153 ± 2344 (0.0002) | 74761 ± 89228 (0.0005) | 41765 ± 52361 (0.0007) |

These results show that the titres of antibodies directed against the influenza virus haemagglutin are increased by a factor of about 10 in the groups subjected to electrical pulses. Thus, the mice which received 1 μg of DNA in the presence of electrical pulses have a mean antibody titre slightly greater than that of the mice which received 10 μg of DNA in the absence of electrical pulse.

The results relating to the titres of antibodies directed against the human cytomegalovirus glycoprotein B are presented in Table 14 B.

TABLE 14B

Titres of antibodies directed against the human cytomegalovirus glycoprotein B (gB), obtained after injection of 10 μg of DNA (VR-gB) in the absence or in the presence of electrical pulses. The results are the geometrical means for 10 animals (9 animals for the group injected in the presence of electrical pulses) ± standard deviation. The value of p was obtained by comparing in pairs the groups injected in the presence and in the absence of electrical pulses using the Man-Whitney nonparametric test

| | Electro-transfer | D 0 | D 21 | D 42 | D 63 |
|---|---|---|---|---|---|
| VR-gB (10 μg) | − | <50 | 73 ± 138 | 755 ± 1766 | 809 ± 1363 |
| VR-gB (10 μg) (p) | + | <50 | 200 ± 119 (0.0558) | 3057 ± 1747 (0.0108) | 2112 ± 1330 (0.0479) |

These results show that the titres of antibodies directed against the human cytomegalovirus glycoprotein B are increased by a factor of 4 at D42, in the group subjected to the electrical pulses. It is also noted that the coefficient of variation is on average three times lower in the groups of animals subjected to the electrical pulses.

What is claimed is:

1. A method of transferring in vivo at least one nucleic acid into one or more tumor cells, comprising:
   (a) administering directly in vivo to said one or more tumor cells said at least one nucleic acid; and thereafter
   (b) electrically stimulating said one or more tumor with least one electric pulse of an electric field intensity ranging from 1 to 600 V/cm to transfer said at least one nucleic acid into said one or more tumor cells, whereafter said transferred at least one nucleic acid is expressed.

2. The method according to claim 1, wherein said electric field intensity ranges from 200 to 600 V/cm.

3. The method according to claim 2, wherein said electric field intensity ranges from 400 to 600 V/cm.

4. The method according to claim 3, wherein said electric field intensity ranges from 500 to 600 V/cm.

5. The method according to claim 1, wherein the electrical stimulation is greater than 10 milliseconds in duration.

6. The method according to claim 1, wherein the electrical stimulation comprises application of said at least one electrical pulse at a regular frequency.

7. The method according to claim 6, wherein the electrical stimulation comprises from 1 to 100,000 pulses.

8. The method according to claim 6, wherein said regular frequency ranges from 0.1 to 1000 hertz.

9. The method according to claim 8, wherein said regular frequency ranges from 0.2 and 100 hertz.

10. The method according to claim 1, wherein the electrical stimulation comprises application of said at least one electrical pulse at an irregular frequency.

11. The method according to claim 10, wherein a function that describes the electric field intensity with time for said at least one electrical pulse is variable.

12. The method according to claim 11, wherein an integral of the function that describes the electric field intensity is greater than 1 kV×msec/cm.

13. The method according to claim 12, wherein the integral is greater than or equal to 5 kV×msec/cm.

14. The method according to claim 1, wherein said at least one electrical pulse is chosen from exponentially decreasing square wave pulses.

15. The method according to claim 1, wherein the electrical stimulation is applied with at least two electrodes placed on either side of a tumor.

16. The method according to claim 1, wherein the electrical stimulation is applied with at least two electrodes introduced inside a tumor.

17. The method according to claim 1, wherein said at least one nucleic acid is injected into a tumor.

18. The method according to claim 1, wherein said at least one nucleic acid is present in a composition comprising pharmaceutically acceptable excipients.

19. The method according to claim 18, wherein said composition is suitable for parenteral administration.

20. The method according to claim 1, wherein said at least one nucleic acid is a deoxyribonucleic acid.

21. The method according to claim 1, wherein said at least one nucleic acid is a ribonucleic acid.

22. The method according to claim 1, wherein said at least one nucleic acid chosen from synthetic nucleic acids, biosynthetic nucleic acids and nucleic acids extracted from viruses, unicellular eukaryotic organisms, pluricellular eukaryotic organisms or prokaryotic organisms.

23. The method according to claim 1, wherein said at least one nucleic acid encodes an RNA or protein of interest.

24. The method according to claim 23, wherein said RNA is a catalytic or antisense RNA.

25. The method according to claim 1, wherein said at least one nucleic acid encodes a protein chosen from enzymes, factor VII, factor VIII, factor IX, complement factors, thrombin, hormones, lymphokines, growth factors, trophic factors, angiogenic factors, neurotrophic factors, bone growth factors, haematopoietic factors, coagulation factors, antigens and proteins involved in the metabolism of amino acids, lipids and other essential constituents of the cell.

26. The method according to claim 25, wherein said at least one nucleic acid encodes a protein chosen from VEGF, FGF, BDNF, CNTF, NGF, IGF, GMF, FGF1, NT3, NT5, the Gax protein, insulin, growth hormone, cytokines, α-I-antitrypsin, calcitonin, leptin, apolipoproteins, and the enzymes for the biosynthesis of vitamins, hormones and neuromediators.

27. The method according to claim 1, wherein said at least one nucleic acid encodes an antibody chosen from a variable fragment of single-chain antibody (ScFv) and other antibody fragments possessing recognition capacities.

28. The method according to claim 27, wherein said antibody is chosen from antiidiotype antibodies, and soluble fragments of the CD4 receptor, the TNFα receptor, and the acetylcholine receptor.

29. The method according to claim 1, wherein said at least one nucleic acid encodes a protein chosen from soluble receptors, agonists of a receptor, antagonists of a receptor, and adhesion proteins for artificial, chimeric and truncated proteins.

30. The method according to claim 1, wherein said at least one nucleic acid encodes a precursor of a protein.

31. The method according to claim 1, wherein said at least one nucleic acid is chosen from plasmids.

32. The method according to claim 1, wherein said at least one nucleic acid comprises at least one gene.

33. The method according to claim 1, wherein said at least one nucleic acid comprises at least one regulatory element.

34. The method according to claim 1, wherein said at least one nucleic acid is chosen from episomal DNA, yeast artificial chromosomes, and minichromosomes.

35. The method according to claim 1, wherein said at least one nucleic acid comprises at least one sequence promoting the expression of a transgene in said at least one tumor cell.

36. The method according to claim 1, wherein said at least one nucleic acid is combined with a composition that aids in the delivery of said at least one nucleic acid to a cell.

37. The method according to claim 36, wherein said composition is chosen from vectors, viruses, synthetic agents, biosynthetic agents, and beads.

38. The method according to claim 1, wherein the quantity of said at least one nucleic acid transferred into said one or more tumor cells is varied by modulating the number of said one or more tumor cells that are contacted.

39. The method according to claim 38, wherein the number of said one or more tumor cells that are contacted is modulated by varying the number sites at which said at least one nucleic acid is administered.

40. The method according to claim 1, wherein the quantity of said at least one nucleic acid transferred into said one or more tumor cells is varied by modulating at least one of the number, shape, surface and arrangement of electrodes.

41. The method according to claim 1, wherein the quantity of said at least one nucleic acid transferred into said one or more tumor cells is varied by modulating at least one of intensity, number, duration, frequency and form of said at least one unipolar pulse.

42. The method according to claim 1, further comprising the step of removing said one or more tumor cells after said at least one nucleic acid has been transferred.

43. The method according to claim 1, wherein said at least one electrical pulse is chosen from square wave pulses.

44. The method according to claim 1, wherein said at least one electrical pulse is chosen from unipolar pulses.

45. The method according to claim 1, wherein said electric field intensity ranges from 100 to 600 V/cm.

46. The method according to claim 1, wherein said at least one electrical pulse is chosen from bipolar pulses.

* * * * *

UNITED STATES PATENT AND TRADEMARK OFFICE
CERTIFICATE OF CORRECTION

PATENT NO. : 6,528,315 B2
DATED : March 4, 2003
INVENTOR(S) : M. Bureau et al.

It is certified that error appears in the above-identified patent and that said Letters Patent is hereby corrected as shown below:

Column 27,
Line 9, "tumor with" should read -- tumor cells with --.
Line 10, before "least", insert -- at --.
Line 10, "electrc pulse" should read -- electrical pulse --.
Line 17, "to 2," should read -- to claim 2, --.
Line 19, "to 3," should read -- to claim 3, --.
Line 64, "acid chosen" should read -- acid is chosen --.

Column 28,
Line 64, "number sites" should read -- number of sites --.

Signed and Sealed this

Eighth Day of July, 2003

JAMES E. ROGAN
Director of the United States Patent and Trademark Office